US012773493B2

(12) United States Patent
Jacobi et al.

(10) Patent No.: US 12,773,493 B2
(45) Date of Patent: Oct. 27, 2026

(54) SYSTEM AND METHOD FOR OPERATING CONTROLLER OF DELIVERY DEVICE HAVING SWIPE AND TAP TO CONFIRM FEATURE

(71) Applicant: Becton, Dickinson and Company, Franklin Lakes, NJ (US)

(72) Inventors: Margaret Anne Jacobi, Newton, MA (US); Sonya Mead, Newton, MA (US); David John Siedzik, Hamilton, MA (US); Tony Hai Nguyen, Hopkinton, MA (US); Ping Zheng, Acton, MA (US); Clinton James Goyette, Princeton, MA (US); Justin David Cumming, Arlington, MA (US); Thomas Frank Kinst, Hillsborough, NJ (US); Marc Clifford Vogt, Rye, NH (US); J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1345 days.

(21) Appl. No.: 16/497,254

(22) PCT Filed: Mar. 22, 2018

(86) PCT No.: PCT/US2018/023725

§ 371 (c)(1),
(2) Date: Sep. 24, 2019

(87) PCT Pub. No.: WO2018/183076

PCT Pub. Date: Oct. 4, 2018

(65) Prior Publication Data

US 2020/0384190 A1 Dec. 10, 2020

Related U.S. Application Data

(60) Provisional application No. 62/478,227, filed on Mar. 29, 2017, provisional application No. 62/478,182, filed on Mar. 29, 2017.

(51) Int. Cl.
*A61M 5/142* (2006.01)
*A61B 5/145* (2006.01)
*G06F 3/04883* (2022.01)

(52) U.S. Cl.
CPC ..... *A61M 5/14244* (2013.01); *A61B 5/14532* (2013.01); *G06F 3/04883* (2013.01); *A61M 2205/505* (2013.01)

(58) Field of Classification Search
CPC ................ A61M 5/14; A61M 5/14244; A61M 5/31546; A61M 60/585; A61M 2005/505;
(Continued)

(56) References Cited

U.S. PATENT DOCUMENTS 6,740,075 B2 * 5/2004 Lebel .................... G06F 3/0673 604/151
D621,849 S 8/2010 Anzures et al.
(Continued)

FOREIGN PATENT DOCUMENTS

CN 101237636 A 8/2008
CN 102495681 A 6/2012
(Continued)

OTHER PUBLICATIONS

Gal Shir, "Water Tracker", Dec. 9, 2015, Dribble. (Year: 2015).*
(Continued)

*Primary Examiner* — Kevin C Sirmons
*Assistant Examiner* — Antarius S Daniel
(74) *Attorney, Agent, or Firm* — Dickinson Wright PLLC

(57) ABSTRACT

A medical device controller is provided that avoids unintended user inputs and unwanted medical device operation(s). A controller sends display commands to a graphical user interface (GUI) display to generate a first screen having a swipe field with no moving icons that prompts a user to initiate a designated operation by the medical device. When
(Continued)

a valid swipe gesture is inputted, the controller generates a second screen with confirm button that requires a valid user press before the controller undertakes the designated operation, the controller generating and sending a command for the designated operation to the medical device when the controller determines that a valid user press has been inputted to the confirm button. The controller also sends commands to generate a status screen that transitions a rotating progress ring symbol and level indicator in accordance with a selected event to clearly indicate the status of medical device operations.

37 Claims, 12 Drawing Sheets

(58) Field of Classification Search
CPC ............ A61M 2205/502; G06F 3/0488; G06F 3/04883
See application file for complete search history.

(56) References Cited

U.S. PATENT DOCUMENTS

| | | | | |
|---|---|---|---|---|
| D626,143 | S | 10/2010 | Karten et al. | |
| D644,661 | S | 9/2011 | Gardner et al. | |
| D644,662 | S | 9/2011 | Gardner et al. | |
| D650,790 | S | 12/2011 | Jeans et al. | |
| D661,314 | S | 6/2012 | Marchetti | |
| D664,987 | S | 8/2012 | Gleasman et al. | |
| D665,421 | S | 8/2012 | Morrow et al. | |
| D669,497 | S | 10/2012 | Lee et al. | |
| D669,499 | S | 10/2012 | Gardner et al. | |
| 8,317,752 | B2 | 11/2012 | Cozmi et al. | |
| D675,639 | S | 2/2013 | Anzures et al. | |
| D675,643 | S | 2/2013 | Frost et al. | |
| D675,644 | S | 2/2013 | Frost et al. | |
| D676,457 | S | 2/2013 | Frost et al. | |
| 8,539,382 | B2 | 9/2013 | Lyon et al. | |
| D690,719 | S | 10/2013 | Thomsen et al. | |
| D691,635 | S | 10/2013 | Ebeling et al. | |
| 8,564,544 | B2 | 10/2013 | Jobs et al. | |
| D698,363 | S | 1/2014 | Asai | |
| D704,216 | S | 5/2014 | Dellinger | |
| D705,793 | S | 5/2014 | Lee | |
| D712,917 | S | 9/2014 | Lee et al. | |
| D715,313 | S | 10/2014 | Hontz, Jr. | |
| D716,325 | S | 10/2014 | Brudnicki | |
| D723,574 | S | 3/2015 | Yamazaki | |
| D727,928 | S | 4/2015 | Allison et al. | |
| 9,041,730 | B2 | 5/2015 | Johnson et al. | |
| 9,071,970 | B2 | 6/2015 | Okuno et al. | |
| 9,077,952 | B2 | 7/2015 | Brodersen et al. | |
| D735,733 | S | 8/2015 | Hontz, Jr. | |
| D739,872 | S | 9/2015 | Bang et al. | |
| D740,855 | S | 10/2015 | Lee et al. | |
| D741,898 | S | 10/2015 | Soegiono et al. | |
| D744,001 | S | 11/2015 | Orr | |
| D745,046 | S | 12/2015 | Shin et al. | |
| D746,855 | S | 1/2016 | Choi | |
| D746,864 | S | 1/2016 | Dellinger | |
| D749,634 | S | 2/2016 | Cho | |
| D750,125 | S | 2/2016 | Yang et al. | |
| D752,640 | S | 3/2016 | Lee | |
| 2003/0060765 | A1* | 3/2003 | Campbell | G16H 40/63 604/131 |
| 2003/0135087 | A1* | 7/2003 | Hickle | G16H 40/63 600/26 |
| 2007/0136679 | A1 | 6/2007 | Yang | |
| 2008/0168404 | A1 | 7/2008 | Ording | |
| 2008/0220752 | A1 | 9/2008 | Forstall et al. | |
| 2009/0209938 | A1* | 8/2009 | Aalto-Setala | G16H 10/65 604/503 |
| 2009/0221890 | A1 | 9/2009 | Saffer | |
| 2010/0156812 | A1 | 6/2010 | Stallings | |
| 2010/0185182 | A1* | 7/2010 | Alme | A61M 5/14276 604/891.1 |
| 2010/0289757 | A1 | 11/2010 | Budelli | |
| 2011/0128244 | A1 | 6/2011 | Cho | |
| 2011/0161811 | A1 | 6/2011 | Choi | |
| 2012/0009896 | A1* | 1/2012 | Bandyopadhyay | G06F 1/1686 715/764 |
| 2012/0096383 | A1 | 4/2012 | Sakamoto et al. | |
| 2012/0200514 | A1* | 8/2012 | Allen | G16H 40/63 345/173 |
| 2012/0238851 | A1 | 9/2012 | Kamen | |
| 2012/0297339 | A1 | 11/2012 | Ito | |
| 2013/0219340 | A1 | 8/2013 | Linge | |
| 2014/0091941 | A1 | 4/2014 | Johnson et al. | |
| 2014/0276419 | A1* | 9/2014 | Rosinko | A61M 5/1723 604/151 |
| 2014/0276531 | A1* | 9/2014 | Walsh | A61M 5/1723 604/151 |
| 2014/0306898 | A1 | 10/2014 | Cueto | |
| 2014/0327629 | A1 | 11/2014 | Jobs et al. | |
| 2014/0331175 | A1* | 11/2014 | Mesguich Havilio | G06F 3/0481 715/863 |
| 2015/0011970 | A1* | 1/2015 | Kamen | G16H 10/65 604/151 |
| 2015/0089439 | A1 | 3/2015 | Wada | |
| 2015/0289823 | A1 | 10/2015 | Rack-Gomer et al. | |
| 2015/0332075 | A1 | 11/2015 | Burch | |
| 2015/0358823 | A1 | 12/2015 | Okuno et al. | |
| 2016/0066843 | A1 | 3/2016 | Mensinger et al. | |
| 2016/0091977 | A1 | 3/2016 | Ortega et al. | |
| 2016/0103604 | A1 | 4/2016 | Johnson et al. | |
| 2016/0106918 | A1 | 4/2016 | Yodfat et al. | |
| 2016/0175517 | A1* | 6/2016 | Sileika | A61M 5/1723 604/504 |
| 2018/0021514 | A1* | 1/2018 | Rosinko | G16H 20/17 604/503 |
| 2018/0193548 | A1* | 7/2018 | Hakansson | G16H 40/63 |

FOREIGN PATENT DOCUMENTS

| | | | | |
|---|---|---|---|---|
| CN | 105144170 A | 12/2015 | | |
| EP | 2 824 554 A1 | 1/2015 | | |
| WO | 2016009499 A1 | 1/2016 | | |
| WO | 2016025036 A1 | 2/2016 | | |
| WO | 2016040423 A1 | 3/2016 | | |
| WO | WO-2017001556 A1 * | 1/2017 | | G06F 3/04847 |

OTHER PUBLICATIONS

My Water Drink Tracker Oy, My Water: Daily Drink Tracker, Feb. 26, 2015, "AppAdvice" (Year: 2015).*

International Search Report dated Jun. 27, 2018, which issued in corresponding PCT Patent Application No. PCT/US2018/023725.

Extended European Search Report dated Dec. 14, 2020, which issued in the corresponding European Patent Application No. 18776860.1.

Chinese Office Action dated Mar. 30, 2021, which issued in the corresponding Chinese Patent Application No. 201880021821.X, including English translation.

* cited by examiner

SYSTEM AND METHOD FOR OPERATING CONTROLLER OF DELIVERY DEVICE HAVING SWIPE AND TAP TO CONFIRM FEATURE

BACKGROUND OF THE INVENTION

Field of the Invention

The present invention relates to medical device controller displays, and more particularly to a medical device controller display that avoids unintended user inputs and corresponding unwanted medical device operation(s) such as inadvertent entry of a command via a button on the device controller's graphical user interface. The present invention also relates to a medical device controller display that clearly indicates to a user the status of the medical device or progress of selected medical device operations.

Description of Related Art

Demand for on-body medical devices (e.g., wearable infusion pumps) and body area network (BAN) medical devices (e.g., handheld blood glucose meters, smart phones with diabetes management apps, and wireless controllers for on-body devices) has been increasing along with an increase in patients' and healthcare providers' desire for better and more convenient patient management of medical conditions such as diabetes. A number of design criteria for user interfaces on on-body medical devices and BAN medical devices should be considered. For example, people who are managing a medical condition using an on-body or BAN device may be suffering a degree of vision, tactile, and/or cognitive impairment. Accordingly, a need exists for a user interface for a medical device that is easy to use, even when the user has some degree of impairment. For example, a need exists for a medical device with display features that are easy to see and understand to clearly indicate to the user the status of the medical device or progress of selected medical device operations, and/or safety features to avoid unintended operations from inadvertent button presses.

SUMMARY OF THE INVENTION

The above and other problems are overcome, and additional advantages are realized, by illustrative embodiments of the present invention.

In accordance with aspects of illustrative embodiments of the present invention, a medical device controller user interface is provided that includes display features that are easy to see and understand to clearly indicate to the user the status of the medical device or progress of selected medical device operations.

For example, it is an aspect of illustrative embodiments of the present invention to provide a system for delivery of a medication to a patient's body, comprising: a device configured to deliver a medication to a patient's body; a controller connected to a medical device and configured to control delivery of medication from the medical device to a patient's body; and a graphical user interface (GUI) display connected to the controller and configured to receive user inputs and provide data relating to the user inputs to the controller and to generate display screens in response to display commands from the controller. The controller is configured to send display commands to the GUI display to generate a first screen having a swipe field over which a user's finger is swiped to receive a user finger swipe gesture and having no moving icons related to the user finger swipe gesture, the swipe field being displayed to prompt a user to initiate a designated operation by the medical device; to send display commands to the GUI display to generate a second screen when the controller has determined from data, which relates to the user finger swipe gesture and is received from the GUI display, that the user finger swipe gesture has traversed a selected amount of the swipe field and in a designated direction along the swipe field to be recognized by the controller as a valid swipe gesture; and to generate and send a command for the designated operation to the medical device when the controller determines that a valid user press has been inputted to a confirm button on the second screen. When the designated operation is delivery of the medication and the controller determines a valid user press has been inputted to a confirm button on the second screen, the controller is configured to command the medical device to initiate delivery of the medication to the patient, and to generate a delivery status screen via the GUI display, the delivery status screen comprising a rotating progress ring symbol and a level indicator, the controller transitioning each of the rotating progress ring symbol and the level indicator in accordance with a selected event related to the delivery of the medication.

In accordance with aspects of illustrative embodiments of the present invention, the user press in the confirm button must occur within a selected time interval after display of the second screen is initiated on the GUI display to be recognized by the controller as a valid user press.

In accordance with aspects of illustrative embodiments of the present invention, the first screen displays alphanumeric screen identifying information indicating the first screen is a swipe to start delivery screen for the controller, and graphical information indicating the designated direction of the valid swipe gesture. For example, the graphical information comprises a series of static arrows pointing in the designated direction of the valid swipe gesture.

In accordance with aspects of illustrative embodiments of the present invention, the controller is configured to send a display command to the GUI display to display a third screen that is a locked screen having a swipe field over which a user's finger is swiped to receive a user finger swipe gesture and having no moving icons related to the user finger swipe gesture, the swipe field being displayed to prompt a user to initiate unlocking the locked screen. In addition, the controller is configured to generate and send display commands to the GUI display to generate a fourth screen when the controller has determined from data, which relates to the user finger swipe gesture and is received from graphical user display, that the user finger swipe gesture has traversed a selected amount of the swipe field and in a designated direction along the swipe field to be recognized by the controller as a valid swipe gesture; and generate and send a command to the GUI display for generating a fifth unlocked screen allowing a designated operation when the controller determines that a valid user press has been inputted to a confirm button on the fourth screen.

In accordance with aspects of illustrative embodiments of the present invention, the third screen displays alphanumeric screen identifying information indicating the first screen is a swipe to unlock screen for the controller, and graphical information indicating the designated direction of the valid swipe gesture. For example, the graphical information comprises a series of static arrows pointing in the designated direction of the valid swipe gesture.

In accordance with aspects of illustrative embodiments of the present invention, the fifth unlocked screen is a start delivery screen configured to allow a user to enter at least one of a request to deliver a dose of medication and an inputted amount of medication, and to require the user to enter a valid press of an button to confirm that delivery of medication is desired.

In accordance with aspects of illustrative embodiments of the present invention, a device for controlling the delivery of a medication to a patient's body, comprises: a controller connected to a medical device and configured to control delivery of medication from the medical device to a patient's body; a user interface connected to the controller and configured to receive user inputs and provide data relating to the user inputs to the controller; and a display connected to the controller and configured to generate display screens. The controller is configured to command the medical device to initiate delivery of the medication to the patient in response to a user input via the user interface, and to generate a delivery status screen via the display in response to the user input. The delivery status screen comprises a rotating progress ring symbol and a level indicator. The controller transitions each of the rotating progress ring symbol and the level indicator in accordance with a selected event related to the delivery of the medication.

In accordance with aspects of illustrative embodiments of the present invention, the controller and the medical device exchange messages, the medical device advising the controller of status of completion of the delivery of the medication, and the controller using the status of completion as the selected event for transitioning each of the rotating progress ring symbol and the level indicator. For example, the status of completion can comprise number of units of the medication delivered to the patient's body. Further, the controller can rotate the progress ring symbol a selected number of degrees corresponding to a selected change in the units of the medication delivered to the patient's body. The progress ring symbol can comprise at least one of a notch along its circumference or a gradient in the thickness of the progress ring symbol to facilitate user discernment of rotation of the progress symbol. The controller can change the level indicator relative to a background image on the display a selected amount corresponding to a selected change in the units of the medication delivered to the patient's body.

In accordance with aspects of illustrative embodiments of the present invention, the controller determines status of completion of the delivery of the medication based on a timer initiated at the initiation of the delivery of the medication, the controller using the amount of time elapsed indicated by the timer as the selected event for transitioning each of the rotating progress ring symbol and the level indicator. For example, the controller rotates the progress ring symbol a selected number of degrees corresponding to the amount of time elapsed indicated by the timer. The progress ring symbol can comprise at least one of a notch along its circumference or a gradient in the thickness of the progress ring symbol to facilitate user discernment of rotation of the progress symbol. The controller can change the level indicator relative to a background image on the display a selected amount corresponding to the amount of time elapsed indicated by the timer. Further, the controller can rotate the progress ring symbol at a rate that transitions the progress ring symbol faster than the changes in the level indicator.

In accordance with aspects of illustrative embodiments of the present invention, the controller is separate from the medical device and connected thereto via wireless communications. For example, the user interface and the display are configured in a graphical user interface (GUI) device. In addition, the GUI device can be on the controller.

In accordance with aspects of illustrative embodiments of the present invention, a user interface is provided that avoids unintended user inputs and corresponding unwanted medical device operation(s), such as inadvertent entry of a command via a button on the device controller's graphical user interface.

For example, it is an aspect of illustrative embodiments of the present invention to provide a device for controlling the delivery of a medication to a patient's body, comprising a controller connected to a medical device and configured to control delivery of medication from the medical device to a patient's body; and a graphical user display connected to the controller and configured to receive user inputs and provide data relating to the user inputs to the controller and to generate display screens in response to display commands from the controller. The controller is configured to send display commands to the graphical user display to generate a first screen having a swipe field over which a user's finger is swiped to receive a user finger swipe gesture and having no moving icons related to the user finger swipe gesture. The controller is configured to generate a second screen when it has determined from data, which relates to the user finger swipe gesture and is received from graphical user display, that the user finger swipe gesture has traversed a selected amount of the swipe field and in a designated direction along the swipe field to be recognized by the controller as a valid swipe gesture, the swipe field being displayed to prompt a user to initiate a designated operation by the medical device. The second screen comprises a confirm button that requires a valid user press before the controller undertakes a designated operation, the controller generating and sending a command for the designated operation to the medical device when the controller determines that a valid user press has been inputted to the confirm button.

In accordance with aspects of illustrative embodiments of the present invention, the user press in the confirm button must occur within a selected time interval after display of the second screen is initiated on the graphical user display to be recognized by the controller as a valid user press.

In accordance with aspects of illustrative embodiments of the present invention, the first screen displays alphanumeric screen identifying information indicating the first screen is a swipe to unlock screen for the controller, and graphical information indicating the designated direction of the valid swipe gesture. For example, the graphical information comprises a series of static arrows pointing in the designated direction of the valid swipe gesture.

In accordance with aspects of illustrative embodiments of the present invention, the first screen displays alphanumeric screen identifying information indicating the first screen is a swipe to start delivery screen for the controller, and graphical information indicating the designated direction of the valid swipe gesture. For example, the graphical information comprises a series of static arrows pointing in the designated direction of the valid swipe gesture.

In accordance with aspects of illustrative embodiments of the present invention, the designated operation indicated by the first screen is a swipe to unlock screen for the controller, and the controller generates a third screen when a valid user press is recognized in the second screen, the third screen being configured to allow a user to enter at least one of a request to deliver a dose of medication and an inputted amount of medication, and to require the user to enter a valid press of an button to confirm that delivery of medication is desired. Further, the controller can generate a fourth screen when a valid press is recognized of the button to confirm that delivery of medication is desired, the fourth screen having a swipe field over which a user's finger is swiped to receive a user finger swipe gesture and having no moving icons related to the user finger swipe gesture. The controller is configured to generate a fifth screen when it has determined from data, which relates to the user finger swipe gesture and is received from graphical user display, that the user finger swipe gesture has traversed a selected amount of the swipe field and in a designated direction along the swipe field to be recognized by the controller as a valid swipe gesture. The fifth screen comprises a confirm button that requires a valid user press before the controller undertakes a designated operation, the controller being configured to command the medical device to deliver medication in response to user input to the fifth screen. The fourth screen can remain displayed by the graphical user display and the fifth screen is not generated when the controller determines that either the user finger swipe gesture has not traversed a selected amount of the swipe field or was in a direction along the swipe field other than the designated direction.

In accordance with aspects of illustrative embodiments of the present invention, the first screen remains displayed by the graphical user display and the second screen is not generated when the controller determines that either the user finger swipe gesture has not traversed a selected amount of the swipe field or was in a direction along the swipe field other than the designated direction.

In accordance with aspects of illustrative embodiments of the present invention, the designated operation can be one of unlock the controller, and command the medical device to deliver medication.

Additional and/or other aspects and advantages of the present invention will be set forth in the description that follows, or will be apparent from the description, or may be learned by practice of the invention. The present invention may comprise a medical device controller and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1:
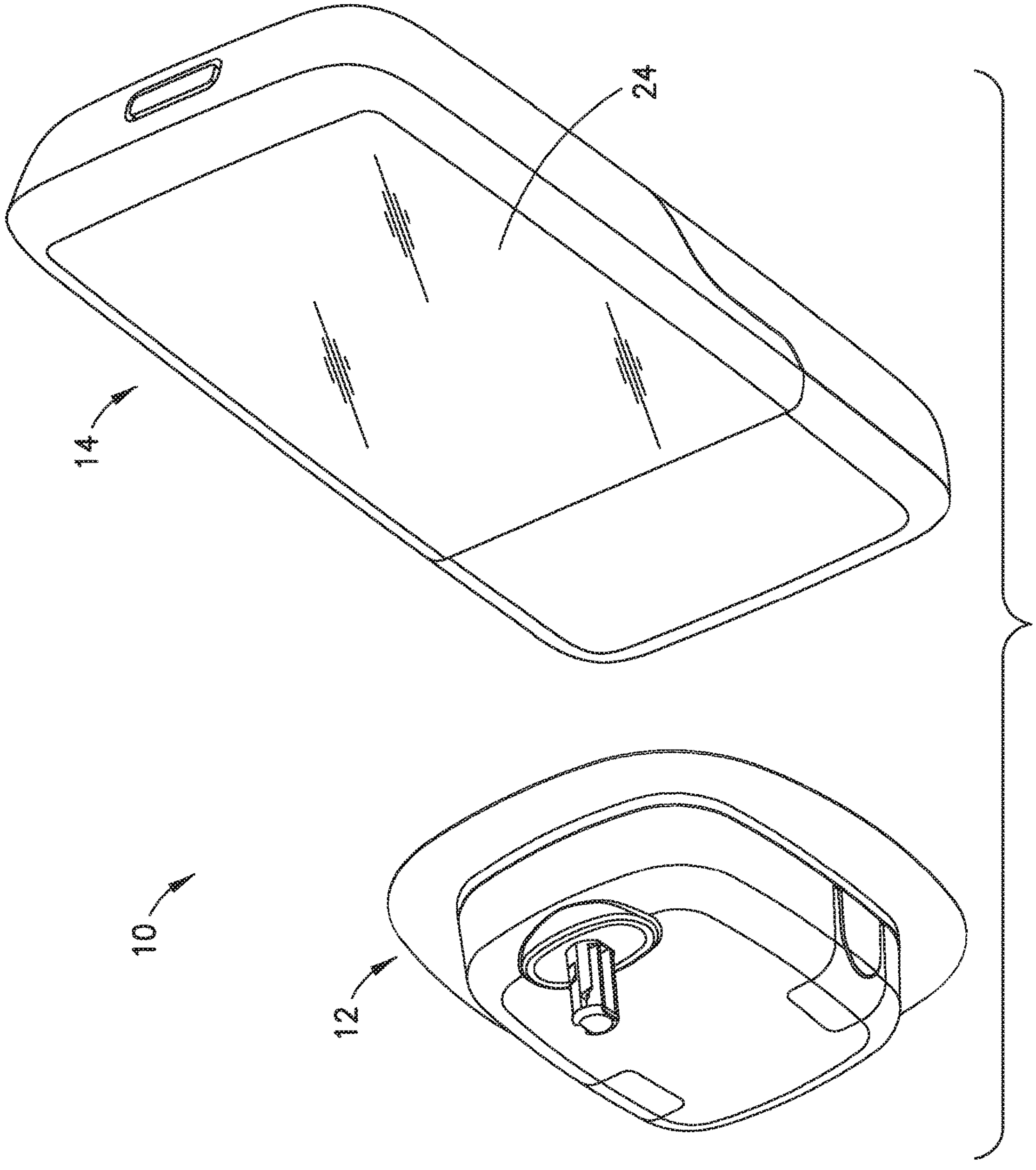
FIG. 1 depicts a medical device and a controller in accordance with an illustrative embodiment of the present invention.

Reference will now be made in detail to embodiments of the present invention, which are illustrated in the accompanying drawings. The embodiments described herein exemplify, but do not limit, the present invention by referring to the drawings.

In accordance with illustrative embodiments of the present invention, a medical device controller with a user interface is provided that realizes a number of advantages comprising, but not limited to, ease of use such as display features that are easy to see and understand to clearly indicate to the user the status of the medical device or progress of selected medical device operations, while avoiding inadvertent user inputs for unintended device operations.

Reference is now made to FIGS. 1 through 13, 14A and 14B, wherein an illustrative medication delivery system 10 is shown having a medical device 12 and a controller 14 with display 24, which is a graphical user interface such as a liquid crystal display (LCD) with touch screen. It is to be understood that, although the example display 24 is shown and described in connection with the controller 14, the display features described here in accordance with example embodiments of the present invention can be provided in a display provided on a medical device, or on a smart phone or other device with display that is used on conjunction with a medical device.

The medical device 12 can be a wearable device or a patient-carried device. The medical device 12 can have an integrated user interface as its controller 14, or the medical device can be configured to be controlled by a separate controller device such as a wireless controller 14 as shown in FIG. 1. In the illustrated embodiment, the medical device 12 is controlled by a wireless controller 14, but it is to be understood that aspects of the present invention apply to a medical device 12 with an integrated user interface and display 24, or a separate controller device 14 with a user interface and display 24 whereby the medical device 12 may or may not have a display 24.

For example, the medical device 12 can be a disposable insulin delivery device (IDD) for single patient use that is configured for continuous subcutaneous delivery of insulin at set and variable basal (24-hour period) rates and bolus (on-demand) doses for the management of patients with Type 2 Diabetes Mellitus (T2DM) requiring insulin therapy. It is to be understood, however, that the medical device 12 can be any on-body medical device (e.g., wearable infusion pump, continuous glucose meter) or body area network (BAN) medical device (e.g., handheld blood glucose meter, smart phone with medical condition management apps, or wireless controller for on-body device).

The IDD 12 is part of a system 10 that is an advanced insulin delivery system for use by patients with Type 2 Diabetes Mellitus (T2DM). It is configured for 24-hour-a-day use in all environments typically inhabited by the target users. It is configured for the patient user to wear the IDD for a period of three days (up to 84 hours). It has four (4) main functions: delivering user-set daily basal insulin rate;

delivering user-set bolus insulin amount; delivering manual bolus insulin dose(s); and generating system status and notifications. The system addresses an unmet need for many Type 2 patients on multiple daily injections (MDI) requiring discreet, simple and cost effective insulin delivery alternative to the traditional complex insulin pump. It is to be understood, however, that the medical device 12 can be used to deliver any type of fluid and is not limited to insulin delivery or to T2 diabetes treatment regimens.

The Wireless Controller (WC) 14 is used to program the body-worn IDD to deliver a daily basal insulin rate and meal-time insulin amount to the patient. The WC 14 also provides status information of the IDD 12 as well as notifications to the user. The body-worn IDD 12 stores and administers insulin to the patient subcutaneously. The IDD sends feedback to the patient via the WC if it detects issues (e.g., low volume in the reservoir, low battery). An important function supported by communication software in the system 10 is the wireless communication between the WC 14 and IDD 12, which enables the IDD 12 to provide the feedback to the WC 14 and for the user to control their insulin delivery by the IDD 12 wirelessly via the WC 14 in a simple and discrete way.

Figure 14A:
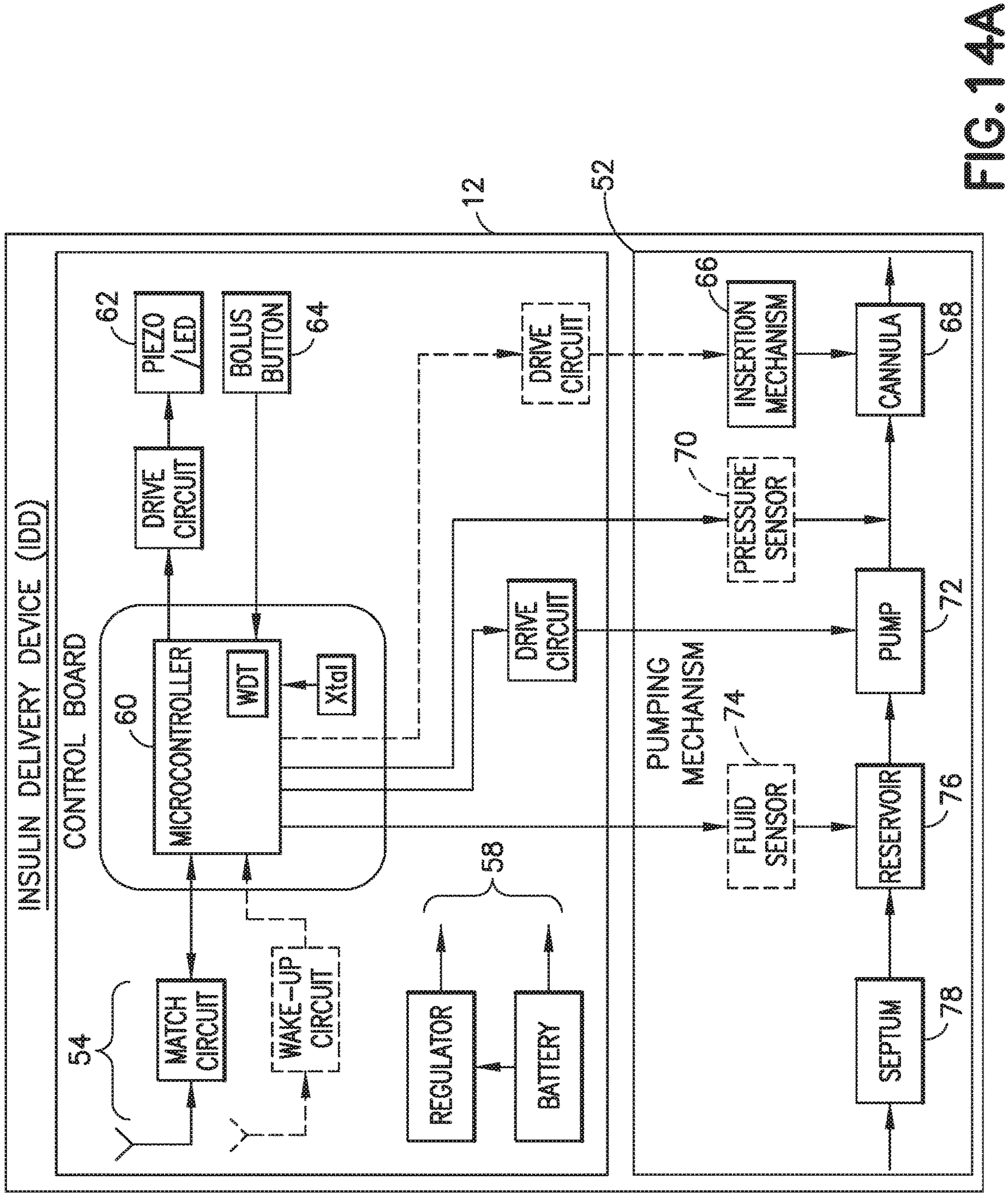
FIGS. 14A and 14B are block diagrams of the medical device and controller in accordance with an illustrative embodiment of the present invention.

In the illustrated embodiment shown in FIG. 14A, the IDD 12 has a microcontroller 60 configured to control a pumping mechanism 52, wireless communication with the WC 14 (e.g., via an RF circuit 54 having a match circuit and antenna), and pump operations. The IDD has a bolus button(s) 64 for manual delivery of medication in addition to programmed delivery of medication. The pumping mechanism 52 comprises a reservoir 76 for storing a fluid medication (e.g., insulin) to be delivered via a cannula 68 to the patient wearing the IDD, and a pump 72 for controllably delivering designated amounts of medication from the reservoir through the cannula. The reservoir 76 can be filled via a septum 78 using a syringe. The IDD has a manual insertion mechanism 66 for inserting the cannula 68 into a patient; however, the processor 60 can be configured to operate an optional drive circuit to automate operation of the insertion mechanism 66 to deploy the cannula 68 into the patient. Further, the IDD 12 can be optionally provided with a fluid sensor 74 or a pressure sensor 70. An LED 62 can be operated by the microcontroller 60 to be on or flash during one or more pump operations such as during reservoir priming, for example. The IDD 12 is powered by a battery and regulator as indicated at 58. When initializing the IDD 12 (e.g., powering on to begin pairing with the WC 12), the bolus button(s) 64 can be configured as wake-up button(s) that, when activated by the user, causes the IDD 12 to wake from a power conserving shelf mode.

Figure 14B:
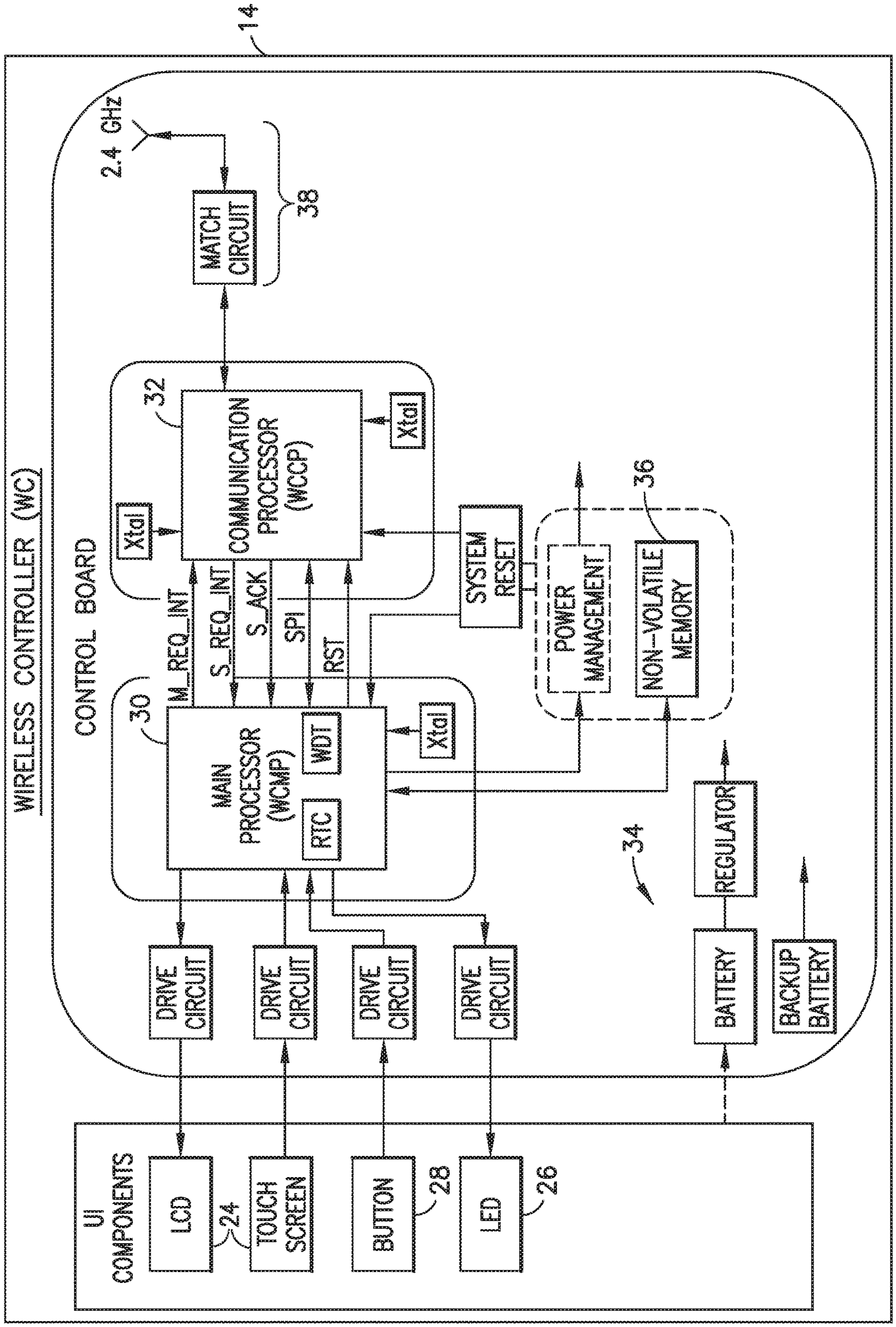

In the illustrated embodiment shown in FIG. 14B, the WC 14 is implemented as a dual microprocessor component having: 1) a WC Main Processor (WCMP) 30, and a WC Communications Processor (WCCP) 32. The WCMP 30 is connected to the user interface (UI) components such as the LCD display with touch screen 24, one or more buttons 28, LED indicator 26, and the like. The WCCP 32 is connected to radio frequency (RF) components 38 (e.g., an antenna and a match circuit) and is mainly responsible for the WC 14's wireless communication with the IDD 12. The two processors 30, 32 communicate with each other through a serial peripheral interface (SPI). The two processors 30, 32 can also interrupt each other through two interrupt pins, M_REQ_INT and S_REQ_INT. It is to be understood that the WC 14 can also be configured as a single processor device.

With continued reference to FIG. 14B, the WC 14 is designed to be non-field serviceable (i.e. no parts to be inspected, adjusted, replaced or maintained by the user), except for replaceable alkaline batteries 34 for power. A non-volatile memory (e.g., FLASH memory) 36 is provided in the WC to store delivery and status data received from the IDD 12 such as delivery dates and times and amounts.

The LCD with capacitive touch screen 24 serves as the visual interface for the user by rendering visual and graphical outputs to the user (e.g., system information, instructions, visual notices, user configurations, data outputs, etc.), and by providing a visual interface for the user to enter inputs (e.g., device operation inputs such as IDD pairing and set up and dosing, and configuration parameters, and so on). The WC display with capacitive touch screen 24 detects (at least) single-touch gestures over its display area. For example, the touch screen is configured for recognizing user tactile inputs (tap, swipe, and button press), allowing for navigation within UI screens (e.g., FIGS. 2 through 13, among others) and applications. The touch screen 24 aids in executing specific system functionalities (i.e. IDD 12 setup and pairing with the WC 14, insulin dosing, providing user with dosing history, and IDD deactivation and replacement with another IDD, and so on) through specific user interactions. The WC 14 can also include a button 28 such as a device wake-up button that, when activated by the user, causes the WC 14 to wake from a power conserving sleep mode. The WC 14 can also have an LED 26 to indicate low battery status (e.g., indicate low battery state when there is 12 hours or less of usage remaining).

The WC 14 radio frequency (RF) interface with the IDD 12 is, for example, based on a Bluetooth Low Energy or BLE-based communication protocol, although other wireless communication protocols can be used. In the medication delivery system 10, the WC 14 and IDD 12 communicate wirelessly within a distance of up to 10 feet or approximately 3 meters, utilizing the ISM band from 2400 MHz to 2480 MHZ spectrum. The WC 14 communicates with the IDD 12 while the IDD is adhered to the body in open air. The WC 14 is the central device or master, and the IDD 12 is the peripheral device or slave. Whenever the WCMP 30 wants to send information to the IDD 12 or retrieve information from the IDD 12, it does so by interacting with the WCCP 32, which in turn, communicates with the IDD 12 across the BLE link via the respective RF circuits 38 and 54.

Figure 15:
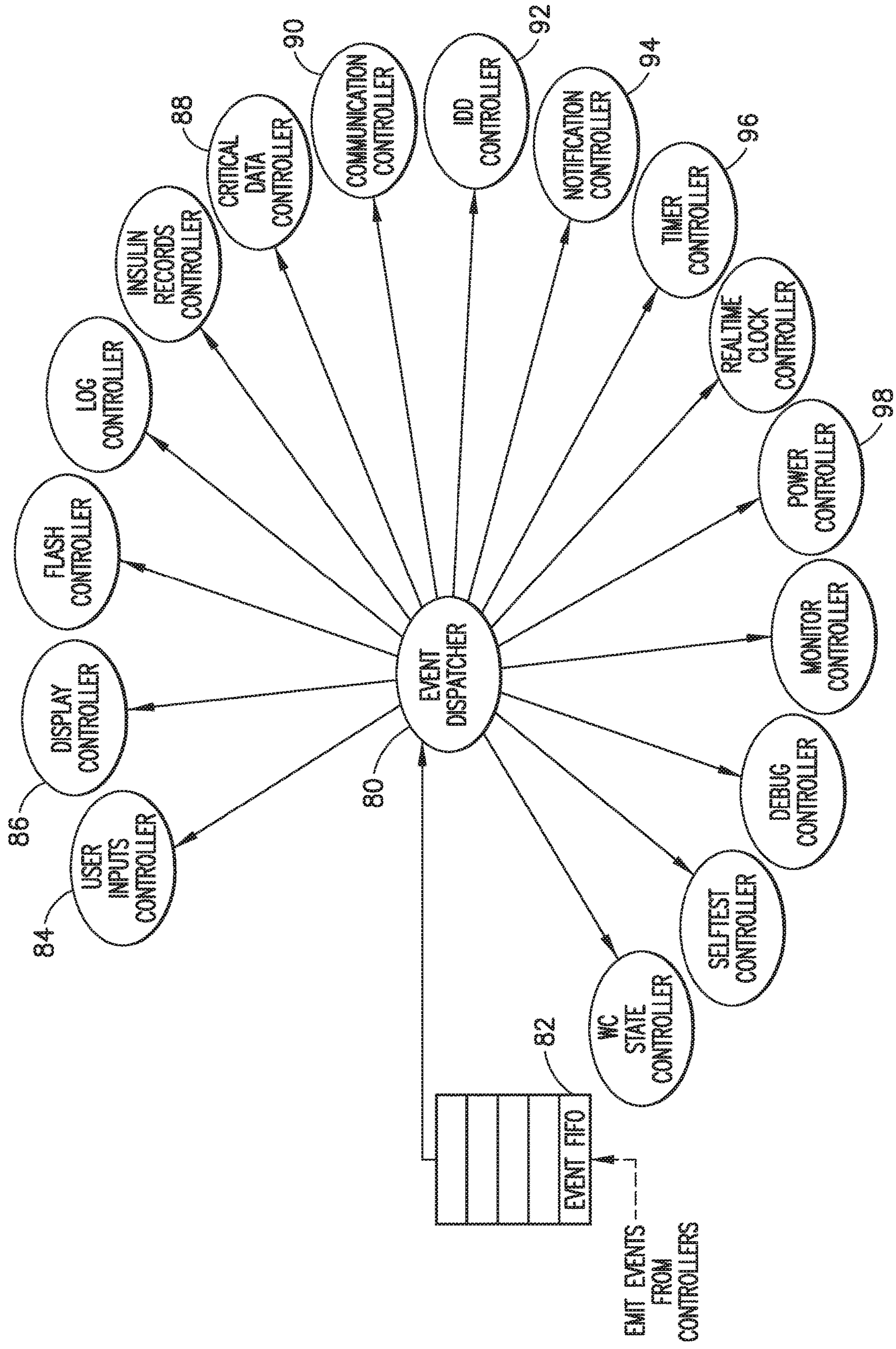
FIG. 15 is a diagram of software architecture of the controller in accordance with an illustrative embodiment of the present invention.

FIG. 15 illustrates a software architecture for the WC 14 in accordance with an illustrative embodiment of the present invention that comprises an Event Dispatcher 80, and a number of Controllers (e.g., 90 and 92), and an Event Queue or FIFO 82 for storing events emitted by the Controllers. It is to be understood, however, that other software architecture can be used for the WC including architecture that does not employ an Event Dispatcher 80 or the Controllers illustrated in FIG. 15.

With continued reference to FIG. 15, a Controller is a bundle of code with a specific responsibility in the WC 14. Controllers work together under direction of the Event Dispatcher 80 to form the WC main application of the WCMP 30. Internally, a Controller module can be composed of many objects/functions that use lower-level interfaces and libraries to achieve its goals. The Controllers communicate by emitting events, such as events that have no associated parameters, and other types of events have specific parameters associated with them. Events can be processed in event first-in-first-out (FIFO) order or First-Emitted, First-Dispatched to be more precise, as indicated at 82.

The Event Dispatcher 80 is configured to give processing time to the Controllers such as by operating as a main loop that calls each of the Controllers once per iteration of the main loop. The Event Dispatcher 80 calls each Controller (a) whenever there is an Event to be processed or (b) whenever an interrupt has occurred while the WCMP 30 is idle. When the Event Dispatcher 80 sees that the Event Queue 82 is empty, it generates an Empty Event Queue Event (EID_NOP). Controllers can use this event to check any hardware they are controlling or ignore it at their discretion. If one or more of the Controllers need to be executed at a periodic rate (e.g. the Display Controller 86 may need to periodically update a progress indicator while a bolus is being delivered), this will be achieved by using the periodic events generated every 100 mS by the Timer Controller 96 described below.

With reference to FIG. 15, the Communications Controller 90 understands the low-level communications protocol (e.g., the SPI between the WCMP 30 and the WCCP 32) and is responsible for handling communications or interactions with the WCCP 32. The Timer Controller 96 is responsible for interactions with various timers employed by the WC 14.

The Critical Data Controller 88 is responsible for managing the critical data that the WC needs to store and for generating checksums, performing reads and writes of ferroelectric random-access memory (FRAM) or other type of memory, for example, and ensuring that the applied protection mechanisms (CRCs, checksums, etc.) will ensure data integrity. The Power Controller 98 is responsible for maintaining the processor 30 in the lowest-possible power mode, retriggering a watchdog timer, adjusting the processor clock speed for normal and low-power modes, and putting the processor 30 into a low-power sleep mode.

Notifications are special conditions that need to be brought to the user's attention. The Notification Controller 94 looks for notifications that are generated by other Controller modules. When it sees that one has occurred, it handles it in the manner dictated for that notification or notification type. To handle the event, the Notification Controller 94 may activate/deactivate various peripherals to cause audible, visual, or tactile feedback to the user. The Notification Controller 94 may generate additional events as required to cause other subsystems to take additional actions.

The User Inputs Controller 84 observes actions taken by the user via the button(s) 28, the touch screen 24, and so on, and generates events that indicate the action that has occurred. The User Inputs Controller 84 generally does not know anything about what touches or gestures are allowed by the current screen or what any of these actions mean to the WC 14.

The Display Controller 86 handles the graphical user interface touch screen display 24 and is responsible for displaying screens to the user and emitting system events (e.g., to the Event Queue of the WCMP 30) based on user interaction with the user interface 24. For example, the Display Controller 86 displays user interface screens, emits events based on user input events (e.g., generated by a User Inputs Controller 84 such as wake button 28 events), emits events based on user inputs generated by a touch screen interface 24, handles processing events that require display updates and/or screen changes, reads critical data (i.e., settings) and displays to the user, and updates user modified data (i.e., settings) to critical data.

The IDD Controller 92 (IDDC) in FIG. 15 is responsible for application-level interactions with the IDD 12 and the WCCP 32. The IDD Controller 92 does this by generating commands and sending these to the Communications Controller 90. After sending a command, the IDDC 92 waits for a response from the WCCP 32 or IDD 12 and processes the response when received. The IDD Controller 92 sends messages to the WCCP 32 in response to events and generates events based on the responses received from the WCCP 32. The IDDC 92 is also responsible for obtaining the status of the WCCP 32 and IDD 12 at the appropriate intervals.

More specifically, after sending a command, the IDD Controller 92 waits for a response and, when received, it processes the application-layer response content. The IDD Controller 92 has no knowledge of the transport-layer and IPC-layer of the messages or the physical interface between the WCMP 30 and the WCCP 32. The IDD Controller 92 is aware that the WCCP 32 is expected to send a response to every command it receives from the WCMP 30. The IDD Controller 92 is also responsible for background communication tasks such as getting WCCP 32 status and IDD 12 status periodically, getting IDD bolus data after a bolus ends, and getting IDD log data prior to deactivation.

The IDD Controller 92 functional responsibilities include, but are not limited to, generate application-layer command events (includes application-layer message content), process application-layer response events, perform sanity checking on the application layer portion of messages, update WC/IDD critical data values, emit bolus record and log data events, and issue periodic IDD status updates. In addition, the IDD Controller 92 manages application-level command/response messaging to perform: pairing, IDD configuration, IDD priming, IDD activation, changing IDD configuration, bolus delivery and cancellation, maintain and display bolus history, deactivation and unpairing of an IDD, and IDD log retrieval, among other operations.

The Display Controller 86 exists as a screen manager containing a global event handler and a screen event handler. The screen manager's global processing event function includes the processing of user input events such as touch screen press, release or swipe events. The screen event handler calls a function to determine if the event is associated with an object on the display that requires display or system interaction and then call a "callback" function for that object. Events that are not associated with any object on the display are ignored. The screen manager also handles the LCD backlight by turning it on or off based on the WC wakeup button events.

For example, the Display Controller 86 contains an internal data structure for each screen containing a list of objects on the screen. If the object has an action associated to it via an event generated by the User Inputs Controller, then a callback function for that object is defined. The following objects have a callback associated with them: (1) button—callback is called if a release or swipe event has been associated with the button; and (2) icon—callback is called if a release event has been associated with the icon.

The screen event handler processes events that are of interest to the screen itself such as a timing event to allow the screen to be displayed for a period of time before transitioning to another screen. Each screen has a unique enumeration identifier along with a ScreenCreate and ScreenProcessEvent function or NULL if no process event function is necessary. The transition from screen to screen is done by a call to a ScreenChange function. The global event handler or local event handler can call the ScreenChange function in order to transition to a new screen.

In accordance with an embodiment of the present invention, a combination of plural touch screens having respective inputs is provided to avoid unintended user inputs and corresponding unwanted medical device operation(s), such as inadvertent entry of a command via a button on the medical device controller's graphical user interface.

Figure 3:
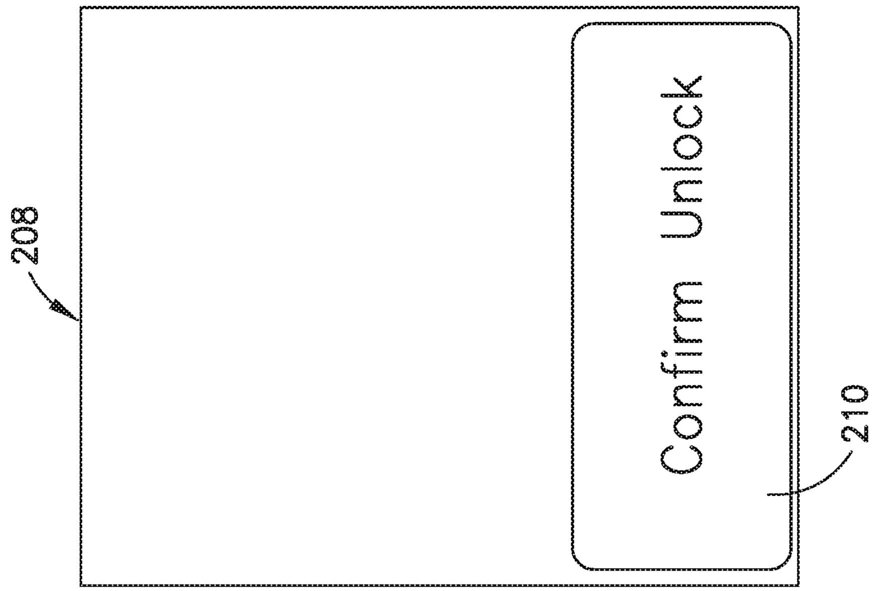
FIGS. 2, 3, 4, 5, 6, 7, 8, 9, 10, 11, 12 and 13 are screens on a medical device controller display in accordance with illustrative embodiments of the present invention.
Figure 2:
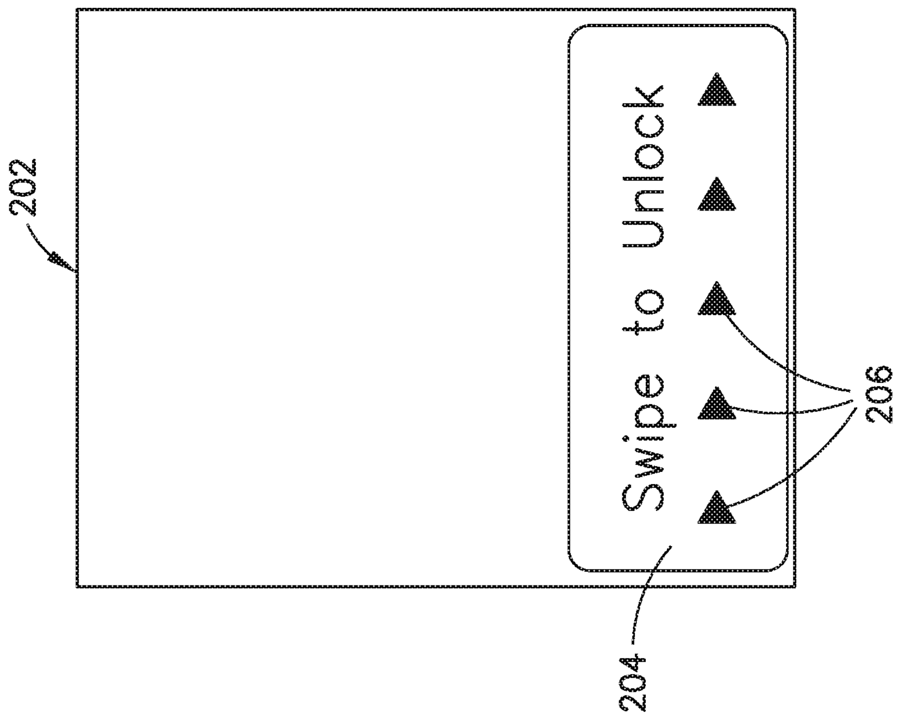
Figure 4:
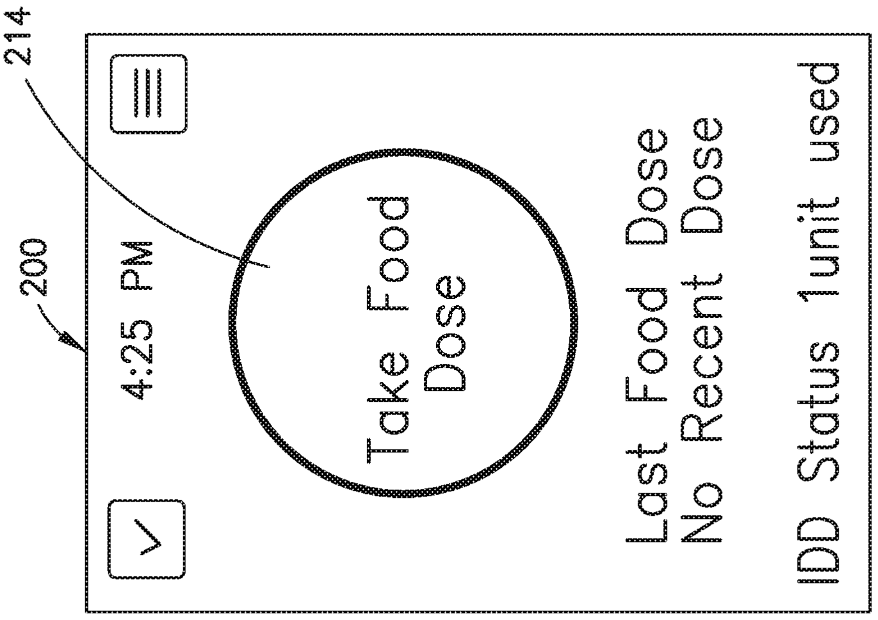

With reference to FIGS. 2 through 7 and 16, illustrative screen images are generated on a display such as the LCD touch screen 24 of the WC 14. As described above, the WCMP 30 is programmed to generate screens on the display 24 in response to various events. For example, if the WC 14 and the IDD 12 are paired, and the IDD 12 has undergone initial setup via the WC 14, a home screen 200 such as that shown in FIG. 4 is displayed. When the WC 14 has not received user input within a selected period of time, the WC 14 enters a lower power sleep mode to conserve WC power (e.g., backlighting of display is off or reduced). For added protection against inadvertent use of the WC, a Swipe to Unlock screen 202 as shown in FIG. 2 is displayed when the WC 14 receives a wake-up input (e.g., via button 28) while in the sleep mode (block 100, FIG. 16). A Swipe to Unlock Button 204 is provided at the bottom of an unlock swipe screen 202.

The Swipe to Unlock Button 204 is configured to only respond when a left-to-right swipe motion that occurs within the button's active area is recognized as a valid swipe gesture by the touch screen 24 hardware and corresponding WCMP 30 software. It is to be understood that the Swipe to Unlock Button 204 can be oriented elsewhere within the area of screen 202 and in a different orientation (e.g., vertical or diagonal versus horizontal). Further, the button 204's active area can be rectangular or other shape. In any event, the slide/swipe field of the Swipe to Unlock button 204 can have static arrows 206 in the button 204 area or adjacent to the button 204 area on the touch screen 24 that are progressively darker shades of color to indicate the direction of swipe gesture needed for user's gesture to be recognized by the screen event handler of the Display Controller 86 as a valid Swipe to Unlock gesture or event. Other static alphanumeric or graphical indicating a direction for a valid swipe gesture. In any event, neither the Swipe to Unlock button 204 nor any part of the Swipe to Unlock screen 202 has any moving image corresponding to the user's finger input. As stated above, the WCMP 30 software is configured to detect when an area of the display 24 designated as representing a "button" (e.g., Swipe to Unlock Button 204) has been pressed or has received a designated gesture (e.g., swipe), and to generate an internal event that allows the WCMP software to respond to the button press or gesture. For example, the Swipe to Unlock button 204 and similar swipe/slide buttons can be configured by the WCMP 30 to require a tactile or capacitive input over a selected percentage of the button 204 area within a designated period of time before an inputted swipe gesture is recognized as valid.

Figure 16:
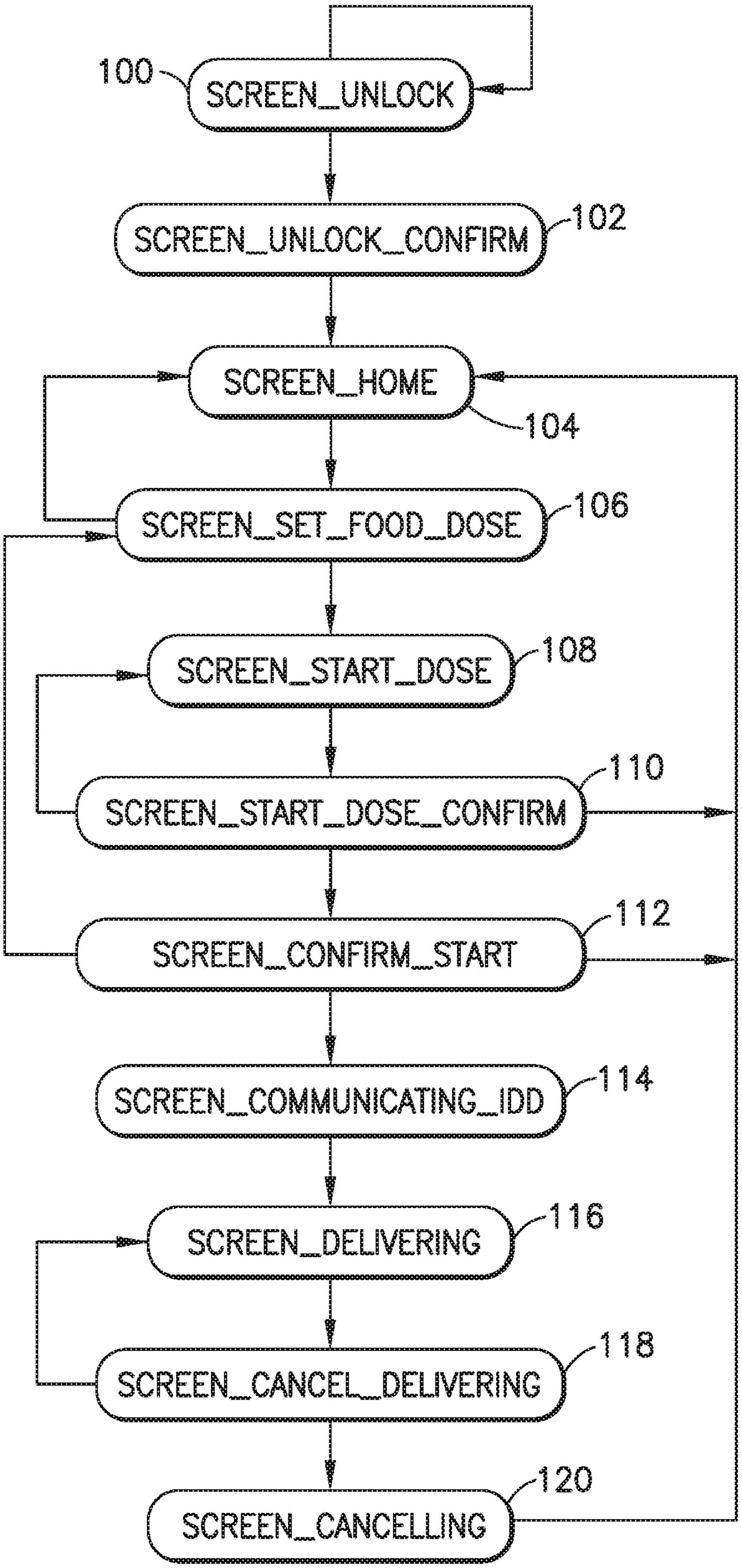
FIG. 16 is a flow chart depicting operations of a medical device controller to guide user inputs in accordance with an illustrative embodiment of the present invention.

With reference to block 102 in FIG. 16, upon recognition of a valid swipe gesture by the Display Controller 86 of the WCMP 30, the graphical user interface (GUI) or touch screen display 24 is transitioned by the WCMP 30 to another screen 208 as shown in FIG. 3, that is, an unlock confirm screen 208, which has a Confirm Unlock Button 210 displayed at the bottom thereof. The screen object (e.g., tap to confirm field 210) can be a rectangle or other GUI button shape into which a user press can be input and recognized as a valid input by the screen manager of the Display Controller 86, although other shapes for the object 210 can be used. In other words, the Confirm Unlock Button 210 responds to a single press and release within the displayed button boundary.

Figure 5:
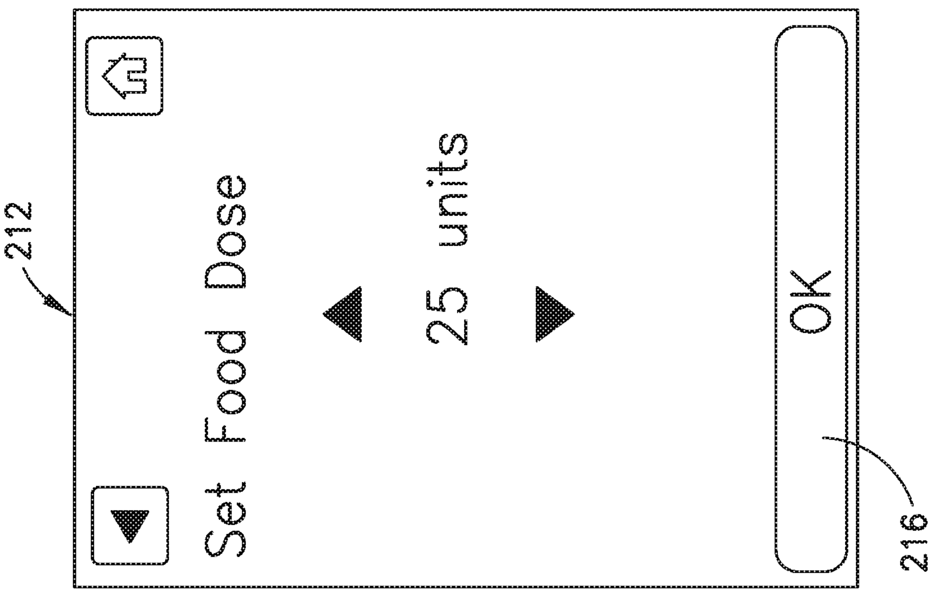

The unlock confirm screen 208 is transitioned to the home screen 200 (FIG. 4 and block 104 in FIG. 16) when a user's gesture in the Confirm Unlock Button 210 is recognized by the Display Controller 86 of the WCMP 30. The home screen 200 has a Take Food Dose button 214 that can be depressed when a user wishes to have a bolus delivered. Upon recognition of a user press of the Take Food Dose button 214, the WCMP 30 is configured to generate a Set Food Dose screen 212 (FIG. 5, block 106 in FIG. 16). When the user inputs a selected dose (e.g., 25 units) into the Set Food Dose screen 212 on the display 24 of the WC 14, the WC 14 communicates the dose to the controller 60 of the IDD 12 to set the pump mechanism 52 accordingly.

When the OK button 216 is pressed (block 108 in FIG. 16), the Display Controller 86 of the WCMP 30 is configured to cause a Swipe to Start screen 218 (FIG. 6, block 110 in FIG. 16) to be generated on the display 24, in accordance with another aspect of illustrative embodiments of the present invention.

The Swipe to Start screen 218 is similar to the Swipe to Unlock screen 202 in that a Swipe to Start button 220 is displayed at the bottom of the screen that is configured to only respond to a left-to-right swipe motion recognized as a valid swipe gesture by the touch screen hardware that occurs within the button's active area. It is to be understood that the Swipe to Start button 220 can be oriented elsewhere within the area of screen 218 and in a different orientation (e.g., vertical or diagonal versus horizontal). Further, the button 220's active area can be rectangular or other shape. In any event, the slide/swipe field or area of the Swipe to Start button 220 can have static arrows 222 in the button 220 area or adjacent to the button 220 area on the touch screen 24 that are progressively darker shades of color to indicate the direction of swipe gesture needed for user's gesture to be recognized by the screen event handler of the Display Controller 86 as a valid Swipe to Start gesture or event. Other static alphanumeric or graphical indicating a direction for a valid swipe gesture. In any event, neither the Swipe to Start button 220 nor any part of the Swipe to Start screen 218 has any moving image corresponding to the user's finger input. As stated above, the WCMP 30 software is configured to detect when an area of the display 24 designated as representing a "button" (e.g., Swipe to Start button 220) has been pressed or has received a designated gesture (e.g., swipe), and to generate an internal event that allows the WCMP 30 software to respond to the button press or gesture.

Figure 7:
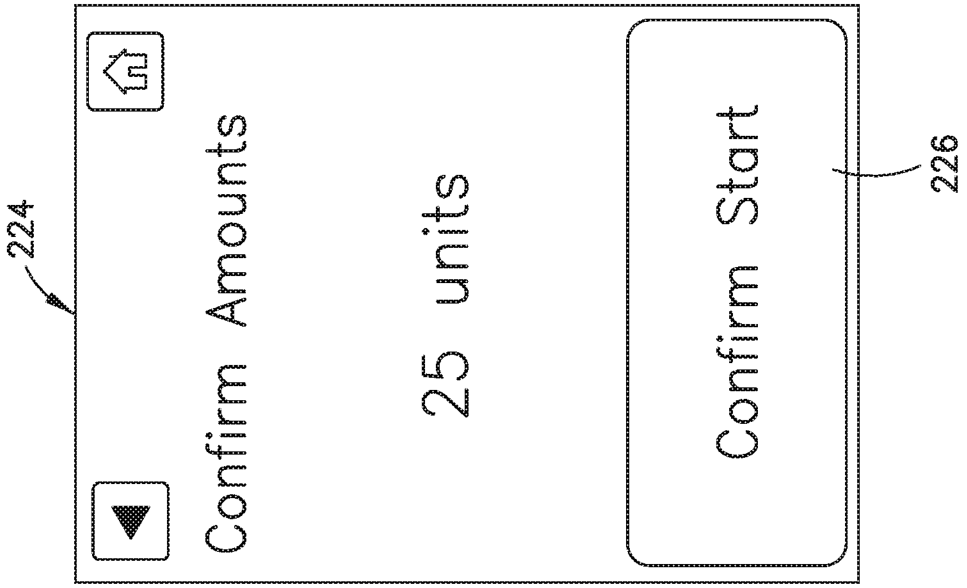
Figure 6:
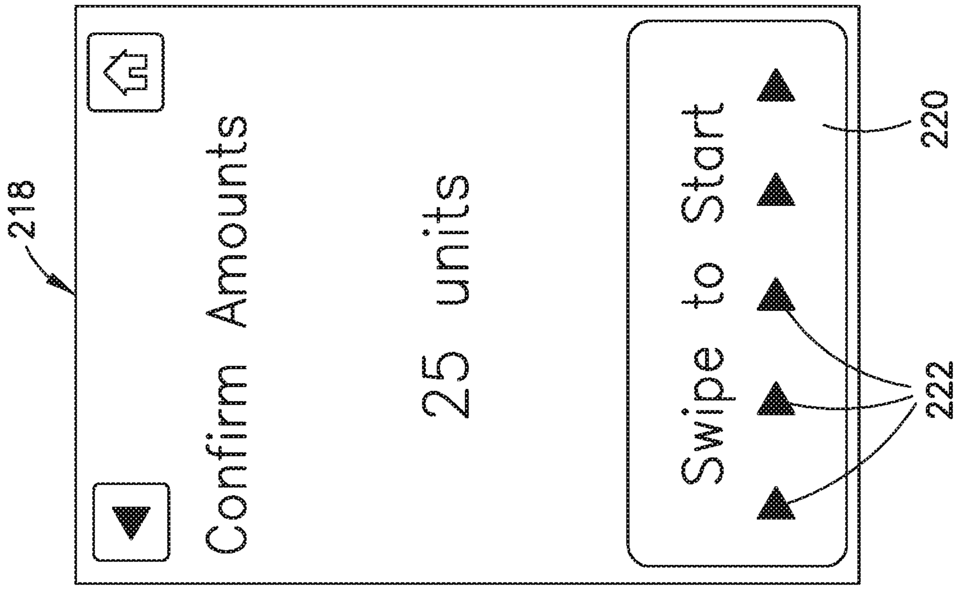
Figure 9:
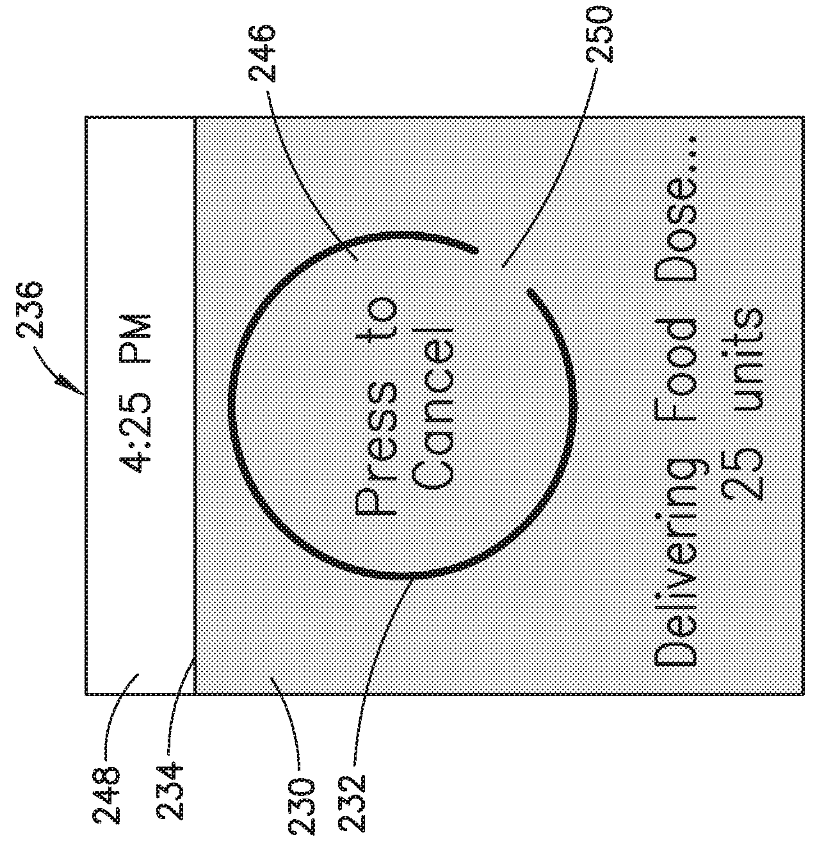

With reference to block 108 in FIG. 16, upon recognition of a valid swipe gesture by the Display Controller 86 of the WCMP 30, the graphical user interface (GUI) or touch screen display 24 is transitioned by the WCMP 30 to another screen 224 as shown in FIG. 7 (block 110 in FIG. 16), that is, an Confirm Start screen 224, which has a Confirm Start button 226 displayed at the bottom thereof. The screen object (e.g., tap to confirm field 226) can be a rectangle or other GUI button shape into which a user press can be input and recognized as a valid input by the screen manager of the Display Controller 86. In other words, the Confirm Start button 226 responds to a single press and release within the displayed button 226 boundary.

The Confirm Start screen 224 is transitioned by the WCMP 30 to a Delivery screen 228 (FIG. 8 and block 114 in FIG. 16) when a user's gesture in the Confirm Start button 226 is recognized by the Display Controller 86 of the WCMP 30 as a valid button press (block 112 in FIG. 16). Thus, inadvertent activation of the WC to commence a dose is avoided by the generation of a first screen requiring a swipe gesture to request a dose, and generation of a second screen with a confirm button only if the swipe gesture in the first screen is valid, and the requirement of a valid press of a confirm button on the second screen before the controller (e.g., WC 14) controls a medical device (e.g., IDD 12) to commence delivery of a medication. Inadvertent activation of the medical device to request a dose or open a home screen or open another screen, after a period of inactivity, is likewise avoided by a similar sequence of screens and gestures (e.g., a swipe on a first screen to unlock the device, a transition to a second screen if a valid swipe gesture is entered, and the valid press of a button on the second screen to confirm unlocking the device). In this manner, inadvertent pressure on the WC 14's display 24 (e.g., a WC being pressed by other items in a user's purse or briefcase or pocket) will not result in inadvertently opening the medical device controller 14 to an operating screen wherein inadvertent changes to settings or unintended device 12 operations can occur as a result of the inadvertent pressure on the controller 14 GUI.

With continued reference to blocks 116, 118 and 120 in FIG. 16, the WC 14 is configured to display a Delivery screen (FIGS. 8 through 12) that indicate status of delivery and provides a user with a touch screen button 246 to cancel delivery, as well as indicate progress of delivery. If the Press to Cancels button 246 receives a valid user activation, then the WC 14 communicates a command to the IDD 12 to stop the pump mechanism 52 from completing the bolus entered by the unit. Upon completion of medication delivery, the WC 14 displays an updated home screen 200 (FIG. 13) with updated dosing information as indicated at 244.

In accordance with embodiments of the present invention and with reference to FIGS. 8 through 12, 17A and 17B, a combination of display screen features are provided to clearly indicate to a user the status of the medical device or progress of selected medical device operations.

Figure 8:
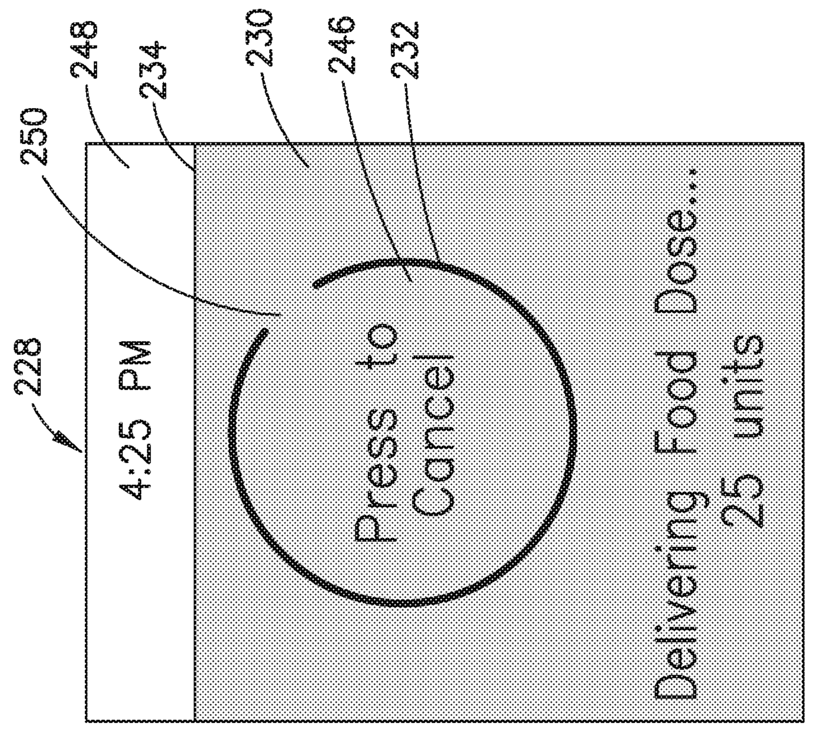
Figure 11:
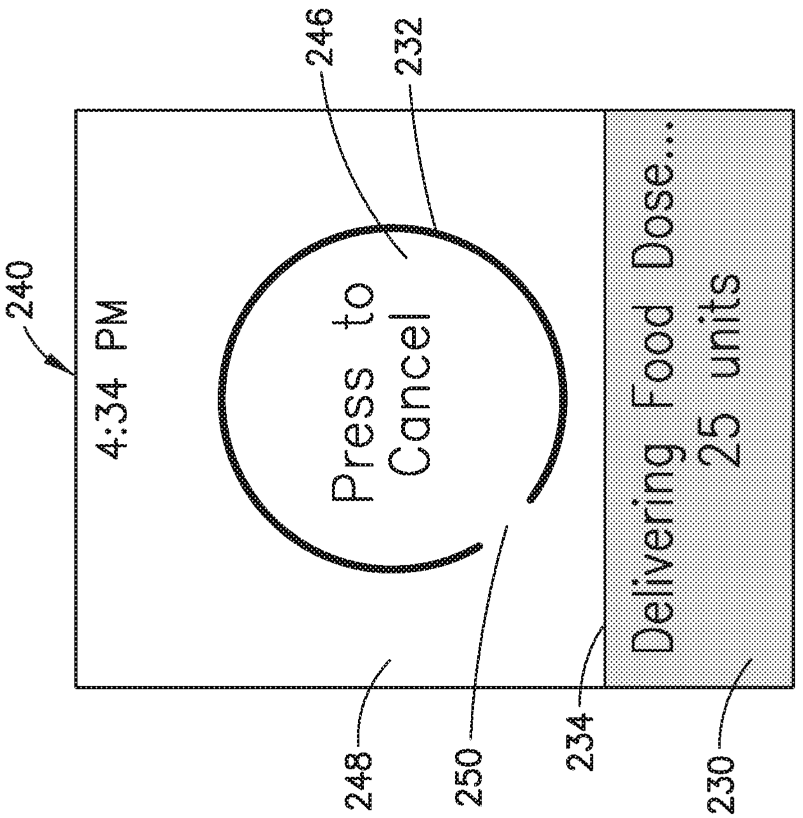
Figure 10:
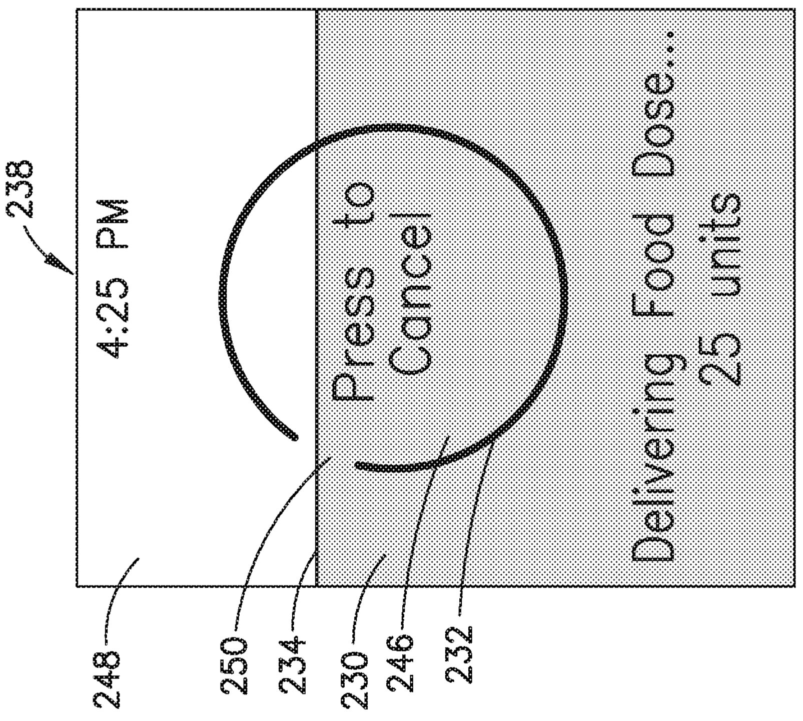
Figure 12:
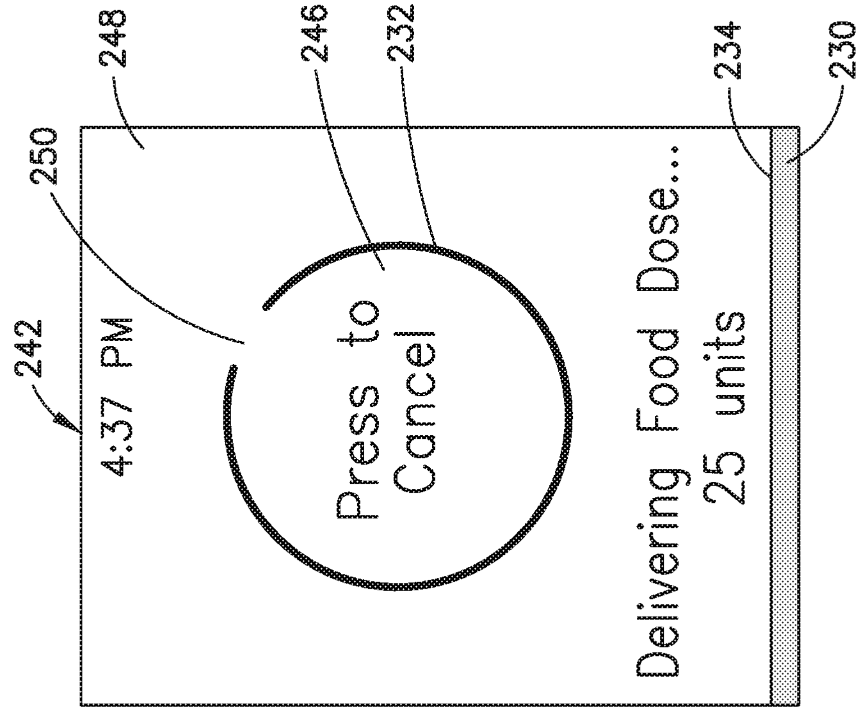
Figure 13:
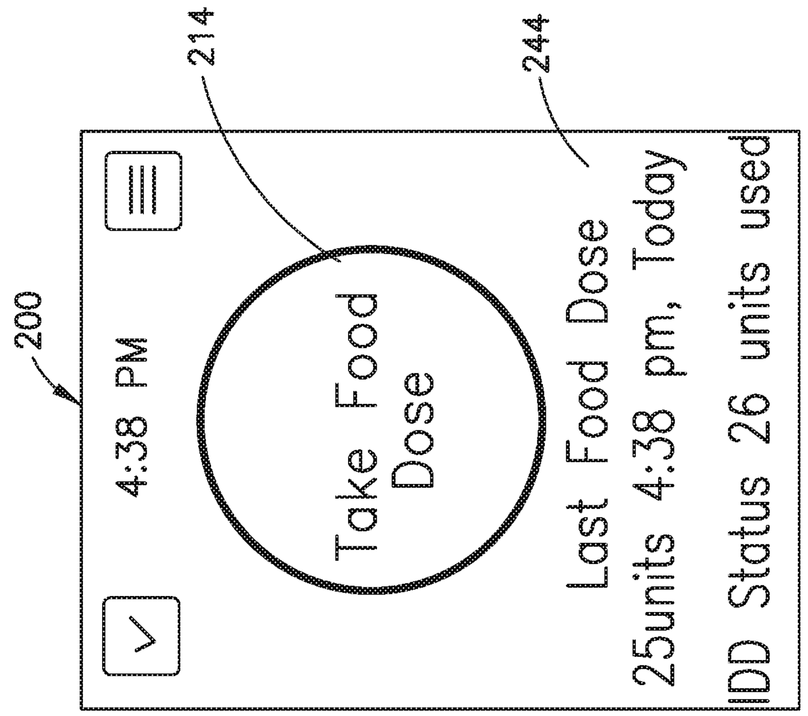

After the Confirm Start button 226 is successfully pressed, a Delivery screen 228 (FIG. 8) is generated by the WCMP 30 as described above. As illustrated in FIG. 8, the Delivery screen 228 comprises two different types of delivery progress indicators, that is, a rotating progress ring 232, and a level indicator 234 (e.g., a background gradient image 230 that transitions as indicated by a transition line 234 delineating the respective background image 248 of the screen and the background gradient image 230, which can be two respective colors are shades of the same color, or different patterns and so on).

For example, upon generation of the Delivery screen 228, the background gradient image 230 can constitute the majority of the area of the display 24 area relative to the background image 248. The WCMP 30 can be configured to update or refresh a screen periodically (e.g., every 1 second or other time interval for screen update). For example, the Delivery screen 228 can be updated such that 10 pixels are overwritten once every update cycle from a background gradient color (e.g., gray as shown in FIGS. 8 through 11) with white or black or other background color that is different from the background gradient color, starting at the top and then down to the bottom of the display. Once less than a selected number of lines from the bottom (e.g. 10 lines) the Delivery screen 228 remain with the background gradient color (e.g., gray), the process starts over such that the background gradient image 230 constitutes the majority of the area of the display 24 area again relative to the background image 248. It is to be understood that other types of level indicators 232 can be used such as a horizontal line on the display 24's Delivery screen 228 that does not involve changing background colors on the display.

In addition to background gradient image 230 transitions described above, the display 24's controller (e.g., WCMP 30) can periodically update a progress indicator 232 while a bolus is being delivered. For the progress indicator 232 (e.g., a ring 232 with notch 250 as shown in FIGS. 8 through 11), can be rotated as indicated by the displacement of the notch 250 as the screen is updated. This update can be accomplished by the Timer Controller 96 emitting a corresponding event at a selected required rate.

The rotations of the progress ring 232 and the background gradient image 230 transitions can be based on different criteria such as by amount of medicament delivered as reported from the IDD 12 to the WC 14 via status messages as described in connection with FIG. 17A, or by time elapsing during delivery as described in connection with FIG. 17B. For example, a background gradient level 234 can be transition (e.g., decreased or lowered, or vice versa increased or raised, before repeating from the top of bottom of the screen respectively) a selected number of pixels per time increment during delivery.

When the background gradient image 230 transitions are based on amount of medication delivered, status messages from the IDD 12 to the WC 14 can be used, that is, status messages from the IDD 12 to the WCMP 14 allow the WCMP to command the Display Controller 86 to change the level 234 of the background gradient image 230 relative to the background image 248 (e.g., by overwriting a selected number of pixels based on a selected number of medication dose increments reported by the IDD 12 has having been delivered).

Figure 17A:
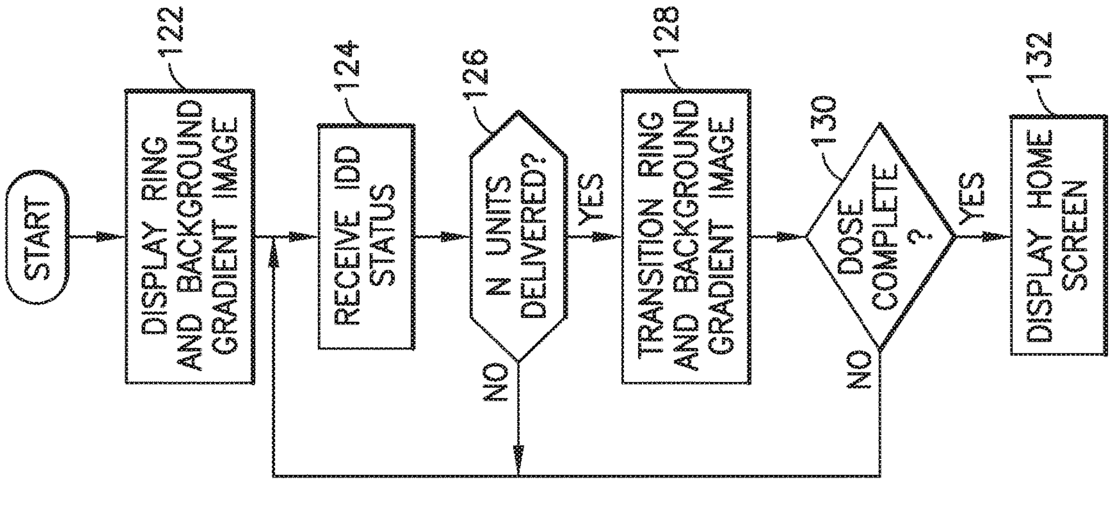
FIGS. 17A and 17B are flow charts depicting operations of a medical device controller to indicate delivery progress in accordance with illustrative embodiments of the present invention.
Figure 17B:
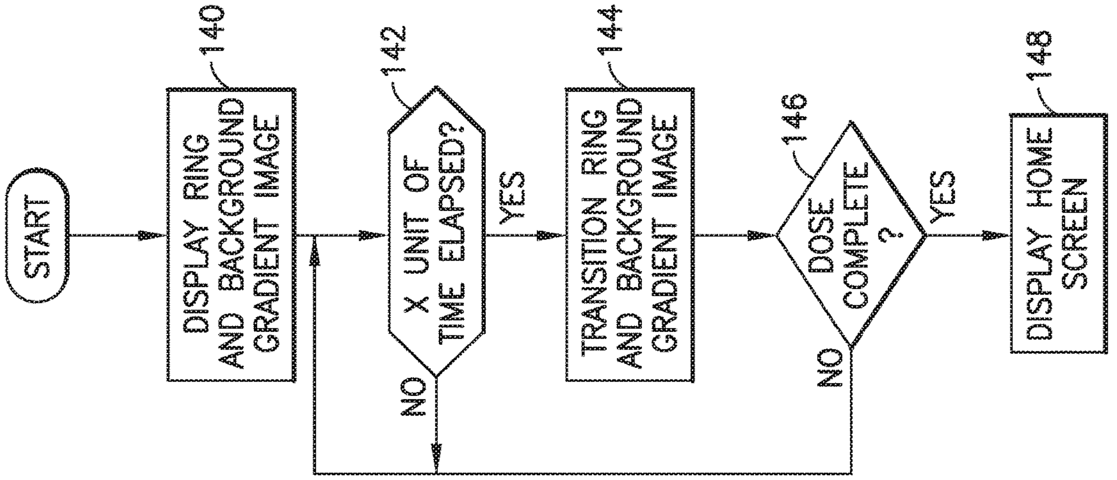

More specifically, as shown in FIG. 17A, a Delivery screen 228 is displayed (block 122). When a user starts a bolus from the WC 14 and while the bolus is running or being delivered, the WCMP 30 polls for IDD status periodically from the IDD 12 by issuing a Get IDD status command (block 124). The IDD response to the Get IDD status command indicates the progress of the bolus delivery, including the number of insulin units delivered and if the bolus has completed (block 126). The WCMP 30 can be configured to transition the background gradient image 230 relative to the background image such as overwrite a selected number of screen lines, and rotate the progress ring 232's notch 250 by a designated number of degrees, based on selected amount of bolus delivered per IDD 12 response or status message (block 128). Upon dose completion (block 130), the WC 14 attempts to retrieve the bolus data by issuing the Get IDD Bolus Data command to the IDD 12. An updated home screen 200 with updated delivery data 244 (FIG. 12) can be displayed (block 132 in FIG. 17A).

Background gradient image 230 and progress ring 232 transitions based on feedback of insulin units delivered can be accomplished with a sufficiently fast processor; otherwise, the background gradient image 230 and progress ring 232 can be transitioned by user discernible increments throughout duration of delivery, whereby the background gradient image 230 transitions repeat top to bottom incremental level 234 changes or vice versa bottom to top incremental level 234 changes. For example, as shown in FIG. 17B, a Delivery screen 228 is displayed (block 140). When a user starts a bolus from the WC 14 and while the bolus is running or being delivered, the WCMP 30 determines how much time elapses since the initiation of the bolus using the Timer Controller and status messages from the IDD 12 indicating whether the bolus delivery is complete (block 142). The WCMP 30 can be configured to transition the background gradient image 230 by a selected number of pixels based on lapsing of selected time increments (block 144). Similarly, the WCMP 30 can be configured to rotate the progress ring 232 to transition the notch 250 by a selected number of degrees based on lapsing of selected time increments (block 144). Upon dose completion (block 146), the WC 14 attempts to retrieve the bolus data by issuing the Get IDD Bolus Data command to the IDD 12. An updated home screen 200 with updated delivery data 244 (FIG. 12) can be displayed (block 148 in FIG. 17B).

In addition, thickness of progress ring can be changed in the same manner. For example, the WCMP 30 can generate a progress ring 232 that thickens based on feedback of amount delivered from the IDD 12 if the microcontroller 30 is a sufficiently fast processor; otherwise, thickening of the progress ring 232 in user discernible increments throughout duration of delivery and repeat ring thickening increments (e.g., make ring 232 thin again, or flash beginning of a new ring 232 that is not yet thickened in place of an existing ring, that is, a new ring at original thickness or partial ring at original thickness) and then gradually thicken, or thicken and fill in a partial ring 232, in increments based on delivery progress or timing. Thus, a notch 250 in the ring 232 would not be needed to discern degree of rotation to indicate progress.

The rotation of the progress ring 232 can be changed or transitioned during the delivery of medication faster relative to the transition of the level indicator 234 to better assist a user to discern that delivery is in progress, even when the level indicator 234 has yet not been transitioned to the next level according to the transitioning criteria used (e.g., a selected number of pixels of display lines per unit delivered or amount of time elapsed since initiation of medication delivery).

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit).

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in the remote station, Electronic medical device, a server, or a combination thereof. In the alternative, the processor and the storage medium may reside as discrete components in a user terminal.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. A system for delivery of a medication to a patient's body, comprising:

a medical device configured to deliver a medication to a patient's body;

a controller connected to the medical device and configured to control delivery of medication from the medical device to a patient's body; and a graphical user interface (GUI) display connected to the controller and configured to receive user inputs and provide data relating to the user inputs to the controller and to generate display screens in response to display commands from the controller;

wherein the controller is configured to control the GUI to generate at least two screens comprising a first screen and a second screen to perform controlling a delivery operation by the medical device;

wherein, for the controlling the delivery operation by the medical device, the controller is configured to send display commands to the GUI display to generate the first screen having a swipe field over which a user's finger is swiped to receive a user finger swipe gesture and having no moving icons related to the user finger swipe gesture, the swipe field being displayed to prompt a user to initiate the delivery operation by the medical device, the swipe field having an active area that is rectangular with a length greater than a width and requires a tactile or capacitive input over at least a selected percentage of the length and in a specified direction along the length and within a designated period of time before an inputted swipe gesture is recognized as valid, send display commands to the GUI display to generate the second screen when the controller has determined from data, which relates to the user finger swipe gesture and is received from the GUI display, that the user finger swipe gesture has traversed at least the selected percentage of the length of the swipe field and in the specified direction along the length of the swipe field and within the designated period of time to be recognized by the controller as a valid swipe gesture, and generate and send a command for the delivery operation to the medical device when the controller determines that a valid user press has been inputted to a confirm button on the second screen;

wherein, when the controller determines a valid user press has been inputted to the confirm button on the second screen, the controller is configured to command the medical device to initiate delivery of the medication to the patient, and to generate a delivery status screen via the GUI display, the delivery status screen comprising a rotating progress ring symbol and a level indicator, the controller transitioning each of the rotating progress ring symbol and the level indicator in accordance with a selected event related to the delivery of the medication, wherein the level indicator comprises a transition line delineating a background image of the delivery status screen and a background gradient image whereby respective portions of the background image and the background gradient image combined constitute an entirety of the delivery status screen generated on the display, and wherein the controller is configured to control movement of the transition line in the delivery status screen to vary the size of the background gradient image displayed relative to the background image, the controller being configured to automatically and incrementally move the transition line and thereby change relative sizes of the respective portions of the background image and the background gradient image during delivery of the medication based on the selected event, the selected event being chosen from amount of the medication being delivered and amount of time elapsed during the delivery of the medication.

2. The system of claim 1, wherein the user press in the confirm button must occur within a selected time interval after display of the second screen is initiated on the GUI display to be recognized by the controller as a valid user press.

3. The system of claim 1, wherein the first screen displays alphanumeric screen identifying information indicating the first screen is a swipe to start delivery screen for the controller, and graphical information indicating the specified direction of the valid swipe gesture.

4. The system of claim 3, wherein the graphical information comprises a series of static arrows pointing in the specified direction of the valid swipe gesture.

5. The system of claim 1, wherein the controller is configured to also perform unlocking the GUI and to send a display command to the GUI display to display a third screen that is a locked screen having another swipe field over which a user's finger is swiped to receive another user finger swipe gesture and having no moving icons in the another swipe field related to the another user finger swipe gesture, the another swipe field being displayed to prompt a user to initiate unlocking the locked screen, the another swipe field having an active area that is rectangular in shape and requires a tactile or capacitive input over a selected percentage of the active area in a specified direction and within a designated period of time before an inputted swipe gesture is recognized as valid.

6. The system of claim 5, wherein the controller is configured to generate and send display commands to the GUI display to generate a fourth screen when the controller has determined from data, which relates to the another user finger swipe gesture and is received from graphical user display, that the another user finger swipe gesture has traversed at least the selected percentage of the length of the another swipe field and in the specified direction along the length of the another swipe field and within the designated period of time to be recognized by the controller as another valid swipe gesture; and generate and send a command to the GUI display for generating a fifth unlocked screen to allow the user to commence user inputs to the GUI to operate the medical device.

7. The system of claim 6, wherein the fifth unlocked screen is a start delivery screen configured to allow a user to enter at least one of a request to deliver a dose of medication and an inputted amount of medication, and that is followed by the first screen and the second screen that requires the user to enter a valid press of the confirm button to confirm that delivery of medication is desired.

8. The system of claim 5, wherein the third screen displays alphanumeric screen identifying information indicating the third screen is a swipe to unlock screen for the controller, and graphical information indicating the specified direction of the another valid swipe gesture.

9. The system of claim 8, wherein the graphical information comprises a series of static arrows pointing in the specified direction of the another valid swipe gesture.

10. The device of claim 1, wherein the background image of the screen and the background gradient image are generated using two different characteristics chosen from two different shades of the same color, two different colors, and two different patterns.

11. The device of claim 1, wherein the progress ring is displayed in the same area of the display wherein the level indicator is moved to alter the amount the background gradient image that is displayed relative to the background image.

12. The device of claim 1, wherein the controller changes the transition line relative to the background image in the delivery status screen to display a selected amount of the background gradient image relative to the background image that corresponds to a selected event chosen from a status of completion of delivery of the medication based on a timer started at the initiation of the delivery of the medication, and a selected change in the units of the medication delivered to the patient's body.

13. A device for controlling the delivery of a medication to a patient's body, comprising a controller connected to a medical device and configured to control delivery of medication from the medical device to a patient's body; and a graphical user interface (GUI) display connected to the controller and configured to receive user inputs and provide data relating to the user inputs to the controller and to generate display screens in response to display commands from the controller;

wherein the controller is configured to generate at least two screens comprising a first screen and a second screen to perform controlling a delivery operation by the medical device;

wherein, for the controlling the designated operation by the medical device, the controller is configured to send display commands to the GUI display to generate the first screen having a swipe field over which a user's finger is swiped to receive a user finger swipe gesture and having no moving icons related to the user finger swipe gesture, the swipe field being displayed to prompt a user to initiate the delivery operation by the medical device, the swipe field having an active area that is rectangular with a length greater than a width and requires a tactile or capacitive input over at least a selected percentage of the length and in a specified direction along the length and within a designated period of time before an inputted swipe gesture is recognized as valid;

wherein the controller is configured to generate the second screen when it has determined from data, which relates to the user finger swipe gesture and is received from GUI display, that the user finger swipe gesture has traversed at least the selected percentage of the length of the swipe field and in the specified direction along the length of the swipe field within the designated period of time to be recognized by the controller as a valid swipe gesture; and wherein the second screen comprises a confirm button that requires a valid user press before the controller undertakes the delivery operation, the controller generating and sending a command for the delivery operation to the medical device when the controller determines that a valid user press has been inputted to the confirm button.

14. The device of claim 13, wherein the user press in the confirm button must occur within a selected time interval after display of the second screen is initiated on the GUI display to be recognized by the controller as a valid user press.

15. The device of claim 13, wherein the first screen displays alphanumeric screen identifying information indicating the first screen is a swipe to start delivery screen for the controller, and graphical information indicating the specified direction of the valid swipe gesture.

16. The device of claim 15, wherein the graphical information comprises a series of static arrows pointing in the specified direction of the valid swipe gesture.

17. The device of claim 13, wherein the controller sends a display command to the GUI to generate a third screen when a valid user press is recognized in the second screen, the third screen being configured to allow a user to enter an inputted amount of medication, and to require the user to enter another valid press of a button on the third screen to confirm that delivery of the inputted amount of medication is desired.

18. The device of claim 13, wherein the first screen remains displayed by the GUI display and the second screen is not generated when the controller determines that either the user finger swipe gesture has not traversed at least the selected percentage of the length of the swipe field or was in a direction along the swipe field other than the specified direction.

19. The device of claim 13, wherein the controller is configured to also perform unlocking the GUI, and to send display commands to the GUI display to generate a third screen that is a locked screen having another swipe field over which a user's finger is swiped to receive another user finger swipe gesture and having no moving icons in the another swipe field related to the another user finger swipe gesture, the another swipe field being displayed to prompt a user to initiate unlocking the locked screen, the another swipe field having an active area that is rectangular in shape and requires a tactile or capacitive input over a selected percentage of the active area in a specified direction and within a designated period of time before an inputted swipe gesture is recognized as valid;

generate a fourth screen when the controller has determined from data, which relates to the another user finger swipe gesture and is received from graphical user display, that the another user finger swipe gesture has traversed at least the selected percentage of the length of the another swipe field and in the specified direction along the length of the another swipe field and within the designated period of time to be recognized by the controller as another valid swipe gesture, the fourth screen comprising a confirm button that requires a valid user press before the controller can generate a fifth screen that is unlocked; and generate the fifth screen to allow the user to commence user inputs to the GUI to operate the medical device.

20. The device of claim 19, wherein the third screen displays alphanumeric screen identifying information indicating the first screen is a swipe to unlock screen for the controller, and graphical information indicating the specified direction of the valid swipe gesture.

21. The device of claim 20, wherein the graphical information comprises a series of static arrows pointing in the specified direction of the valid swipe gesture.

22. A device for controlling the delivery of a medication to a patient's body, comprising a controller connected to a medical device and configured to control delivery of medication from the medical device to a patient's body;

a user interface connected to the controller and configured to receive user inputs and provide data relating to the user inputs to the controller; and a display connected to the controller and configured to generate display screens, each of the display screens constituting a defined area on the display;

wherein the controller is configured to command the medical device to initiate delivery of the medication to the patient in response to a user input via the user interface, and to generate a delivery status screen via the display in response to the user input;

wherein the delivery status screen comprises a rotating progress ring symbol and a level indicator, the controller transitioning each of the rotating progress ring symbol and the level indicator in accordance with a selected event related to the delivery of the medication; and wherein the level indicator comprises a transition line delineating a background image of the delivery status screen and a background gradient image whereby respective portions of the background image and the background gradient image combined constitute an entirety of the delivery status screen generated on the display, wherein the controller is configured to control movement of the transition line in the delivery status screen to vary the size of the background gradient image displayed relative to the background image, the controller being configured to automatically and incrementally move the transition line and thereby change relative sizes of the respective portions of the background image and the background gradient image during delivery of the medication based on the selected event, the selected event being chosen from amount of the medication being delivered and amount of time elapsed during the delivery of the medication, and wherein the progress ring is superimposed on the respective portions of the background image and the background gradient image that combined constitute the entirety of the delivery status screen generated on the display such that the progress ring is displayed simultaneously in the defined area with the level indicator and overlaps any of the background image and the background gradient image and the transition line depending on where the level indicator is moved to alter the amount the background gradient image that is displayed relative to the background image.

23. The device of claim 22, wherein the controller and the medical device exchange messages, the medical device advising the controller of status of completion of the delivery of the medication, and the controller using the status of completion as the selected event for transitioning each of the rotating progress ring symbol and the level indicator.

24. The device of claim 23, wherein the status of completion comprises number of units of the medication delivered to the patient's body.

25. The device of claim 24, wherein the controller rotates the progress ring symbol a selected number of degrees corresponding to a selected change in the units of the medication delivered to the patient's body.

26. The device of claim 25, wherein the progress ring symbol comprises at least one of a notch along its circumference or a gradient in the thickness of the progress ring symbol to facilitate user discernment of rotation of the progress symbol.

27. The device of claim 24, wherein the controller changes the position of the level indicator relative to the background image in the delivery status screen to display a selected amount of the background gradient image to correspond to a selected change in the units of the medication delivered to the patient's body.

28. The device of claim 22, wherein the controller determines status of completion of the delivery of the medication based on a timer initiated at the initiation of the delivery of the medication, the controller using the amount of time elapsed indicated by the timer as the selected event for transitioning each of the rotating progress ring symbol and the level indicator.

29. The device of claim 28, wherein the controller rotates the progress ring symbol a selected number of degrees corresponding to the amount of time elapsed indicated by the timer.

30. The device of claim 29, wherein the progress ring symbol comprises at least one of a notch along its circumference or a gradient in the thickness of the progress ring symbol to facilitate user discernment of rotation of the progress symbol.

31. The device of claim 29, wherein the controller rotates the progress ring symbol at a rate that transitions the progress ring symbol faster than the changes in the level indicator.

32. The device of claim 28, wherein the controller changes the level indicator relative to the background image in the delivery status screen to display a selected amount of the background gradient image relative to the background image that corresponds to the amount of time elapsed indicated by the timer.

33. The device of claim 22, wherein the controller is separate from the medical device and connected thereto via wireless communications.

34. The device of claim 22, wherein the user interface and the display are configured in a graphical user interface (GUI) device.

35. The device of claim 34, wherein the GUI device is on the controller.

36. The device of claim 22, wherein the controller determines status of completion of the delivery of the medication based on a timer initiated at the initiation of the delivery of the medication, the controller using the amount of time elapsed indicated by the timer as the selected event for transitioning each of the rotating progress ring symbol and the level indicator; and wherein the controller changes the level indicator relative to a background image in the delivery status screen to display a selected amount of the background gradient image relative to the background image that corresponds to the amount of time elapsed indicated by the timer.

37. The device of claim 22, wherein the background image of the delivery status screen and the background gradient image are generated using two different characteristics chosen from two different shades of the same color, two different colors, and two different patterns.

* * * * *